(12) United States Patent
Ziv et al.

(10) Patent No.: US 7,396,859 B2
(45) Date of Patent: Jul. 8, 2008

(54) PERTURBED MEMBRANE-BINDING COMPOUNDS

(75) Inventors: Ilan Ziv, Kfar Saba (IL); Anat Shievan, Herzliya (IL); Sharon Ebner, Raanana (IL)

(73) Assignee: NST Neurosurvival Technologies, Ltd., Petah-Tikva (IL)

( * ) Notice: Subject to any disclaimer, the term of this patent is extended or adjusted under 35 U.S.C. 154(b) by 232 days.

(21) Appl. No.: 10/433,668

(22) PCT Filed: Dec. 3, 2001

(86) PCT No.: PCT/IB01/02282

§ 371 (c)(1),
(2), (4) Date: Oct. 31, 2003

(87) PCT Pub. No.: WO02/46147

PCT Pub. Date: Jun. 13, 2002

(65) Prior Publication Data

US 2004/0082499 A1    Apr. 29, 2004

(30) Foreign Application Priority Data

Dec. 6, 2000 (IL) ..................... 140114
Feb. 21, 2001 (IL) ..................... 141571
Aug. 30, 2001 (IL) ..................... 145210

(51) Int. Cl.
*A01N 37/12* (2006.01)
*A01N 37/44* (2006.01)

(52) U.S. Cl. .................................. 514/562
(58) Field of Classification Search .............. 514/1, 514/562; 562/427
See application file for complete search history.

(56) References Cited

U.S. PATENT DOCUMENTS 5,399,501 A * 3/1995 Pope et al. ............... 436/532

FOREIGN PATENT DOCUMENTS

EP          451 824 A2       10/1991
SU          1686373       *  10/1991
WO          WO 99/27921   *  6/1999

OTHER PUBLICATIONS

Atchanassakis et al., Journal of Receptors and Signal Transduction Research, 1999, 19(1-4), 143-154.*
Verga et al., Mechanism of Allergic Cross-reactions I Multispecific Binding of Ligands to a Mouse Monoclonal Anti-DNA IgE Antibody, Molecular Immunology, 1991, 28(6), 641-54.*
Monogrodsky et al., Inhibition of pokeweed Mitogen-induced B Cell Differentiation by Compounds Containing Primary Amine or Hydrazine Groups, Clinical and Experimental Immunology, 1985, 59(1), 69-76.*

Olive et al., Characterization of the uptake and toxicity of a fluorescent thiol reagent (p. 349-353), Cytometry, 3, (5) 1982.*
Rice, G, et al., "Use of N-Σ- dansyl-L-lysine and flow cytometry to identify heat-killed mammalian cells" Int. J. Hyperthermia 1, pp. 185-191 (1985).
Rehse, K, et al., "Oligoamines with Fluorescent Properties, Part B: Fluorophores in the Molecular Periphery". Arch. Pharm. 327, pp. 399-404 1994.
Muczynski, K, et al., "Incorporation of Dansylated Phospholipids and Dehydroergosterol into Membranes Using a Phospholipid Exchange Protein" Biochemistry 22, pp. 6037-6048 (1983).
Sekiguchi, R, et al., "The use of Dansyl Lysine to assess heat damage and theromotolerance of normal tissues" I.J. Radiation Oncology Biol. Phys. 14, pp. 983-988 (1988).
Epps, D, et al., "Determination of Dissociation Constants of High Affinity (pM) Human Renin Inhibititos: Application to Analogues of Ditekiren" J. Med. Chem. 34, pp. 2107-2112 (1991).
Fratazzi, C, et al., "Programmed Cell Death of *Mycobacterium avium* Serovar 4- Infected Human Macrophages Prevents the Mycobacteria from Spreading and Induces Mycobacterial Growth Inhibition by Freshly Added, Uninfected Macrophages" Journal of Immunology 158, pp. 4320-4327 (1997).
Selir,N, et al., "Polyamine sulfonamides with NMDA antagonist properties are potent calmodulin antagonists and cytotoxic agents" The International Journal of Biochemistry & Cell Biology 30 pp. 393-406 (1998).
Rodgers,G, et al., "Formation of Factor Va by Atherosclerotic Rabbit Aorta Mediates Factor Xa -catalyzed Prothrombin Activation" Journal Clinical Invest. 81, pp. 1911-1919 (1988).
Callaghan, R, et al., "A comparison of membrane properties and composition between cell lines selected and tranfected for multi-drug resistance" Br. J. Cancer 66, pp. 781-786 (1992).
Taylor Jr., F.B., et al., " DEGR-Factor Xa Blocks Disseminated Intravascular Coagulation Initiated by *Escherichia coli* Without Preventing Shock or Organ Damage."Blood 178, pp. 364-368 (1991).
Hirose, K, et al., "Activated Protein C Reduces the Ischemia/Reperfusion-Induced Spinal Cord Injury in Rats by Inhibiting Neutrophil Activation" Annals of Surgery 232, pp. 272-280 (2000).
Humphries, G, et al., "Cholesterol-Free Phospholipid Domains May be The Membrane Feature selected by N-Σ-Dansyl-L-Lysine and Merocyanine 540" Biochemical and Biophysical Research Communications 111, pp. 768-774 (1983).
Robson, C, et al., "Chemical Synthesis and Biological Properties of Novel Fluorescent Antifolates in Pgp and MRP Overexpressing Tumor Cell Lines" Biochemical Pharmacology 56, pp. 807-816 (1998).

(Continued)

*Primary Examiner*—Yvonne Eyler
*Assistant Examiner*—Chukwuma O Nwaonicha
(74) *Attorney, Agent, or Firm*—The Nath Law Group; Susanne M. Hopkins; Ari G. Zytcer

(57) ABSTRACT

The present invention provides uses of compounds that bind selectively to cells undergoing perturbations and alterations of their normal membrane organization, while binding to a lesser degree to cell having membranes of normal organization. These compounds are termed perturbed-membrane-binding compounds (PMBC). The PMBC group of compounds includes new compounds and also known compounds.

4 Claims, 7 Drawing Sheets

OTHER PUBLICATIONS

Berlot, J.P., et al., "Preparation of a dansylated fibrate, a new fluorescent tool to study peroxisome proliferation. Effect on hepatic-derived cell lines" Biochimie 79, pp. 145-150 (1997).

Hayakawa, M, et al., " Effects of mono dansyl cadaverine on platelet aggregations, blood coagulations and erythrocyte deformabilities" Japanese Journal of Geriatrics. 22, pp. 144-150 (Mar. 2, 1985) XP01127498.

Stary, H, et al., "A Definition of Advanced Types of atherosclerotic Lesions and a Histological Classification of Atherosclerosis" Circulation 92, pp. 1355-1374 (1995).

Van den Eijnde, S, et al., "Phosphatidylserine plasma membrane asymmetry in vivo: a pancellular phenomenon which alters during apoptosis" Cell Death and Differentiation 4, pp. 311-316, (1997).

Sims, P, et al., "Unraveling the Mysteries of Phospholipid Scrambling" Thromb Haemost 86, pp. 266-275 (2001).

Pugsley, P, et al., "The Impact of Microemboli During Cardiopulmonary Bypass on Neuropsychological Functioning" Stroke 25, pp. 1393-1399 (1994).

Martin, J, et al., "Early Redistribution of Plasma Membrane Phosphatidylserine is a General Feature of Apoptosis Regardless of the Initiating Stimulus: Inhibition by Overexpression of Bcl-2 and Abl" J. Exp. Med. 182, pp. 1545-1556 (1995).

Mallat, Z, et al., "Colocalization of Cpp-32 with Apoptotic Cells in Human Atherosclerotic Plaques" Circulation 96, pp. 424-428 (1997).

Kockx, M, et al., "Apoptosis atherosclerosis: beneficial or detrimental?" Cardiovascular Research 45, pp. 736-746 (2000).

Bursch, W, et al., "Cell death by apoptosis and its protective role against disease" TiPS 13, pp. 245-251 (1992).

Bratton, D, et al., "Appearance of Phosphatidylserine on Apoptotic Cells Requires Calcium-mediated Nonspecific Flip-Flop and Is Enhanced by Loss of the Aminophospholipid Translocase" The Journal of Biological Chemistry 272, pp. 26159-26165 (Oct. 17, 1997).

Bombeli, T, et al., "Apoptotic Vascular Endothelial Cells Become Procoagulant" Blood 89, pp. 2429-2442 (1997).

Bevers, E, et al., "Lipid translocation across the plasma membrane of mammalian cells" Biochimica et Biophysica Acta 1439, pp. 317-330 (1999).

Olive, P.L., et al. "Characterization of the Uptake and Toxicity of a Fluorescent Thiol Reagent", *Cytometry*, vol. 3, No. 5, p. 349-353, (1982).

Lazarides, E., et al. "Fluorescent localization of membrane sites in glycerinated chicken skeletal muscle fibers and the relationship of these sites to the protein composition of the Z disc", Biochemistry, vol. 75, No. 8, p. 3683-3687, (Aug. 1978) .

Hochstrate, P., et al. "On the evaluation of Photoreceptor Properties by Micro-Fluorimetric Measurements of Fluorochrome Diffusion", *Biophysic of Structure and Mechanism*, vol. 6, p. 125-138, (1980).

Hammermeister, D.E., et al. "Characterization of dansylated glutathione, glutathione disulfide, cysteine and cystine by narrow bore liquid chromatography/electrospray ionization mass spectrometry", *Rapid Communications in Mass Spectrometry*, vol. 14, p. 503-508, (2000).

* cited by examiner

PERTURBED MEMBRANE-BINDING COMPOUNDS

FIELD OF THE INVENTION

The present invention relates to novel compounds, pharmaceutical compositions and novel therapeutic and diagnostic methods using same.

LIST OF REFERENCES

The following references are considered to be pertinent for the purpose of understanding the background of the present invention:

Bevers, E. M., et al., *Biochim. Biophys. Acta,* 1439:317-330, 1999;
Bombeli, T., et al., *Blood,* 89:2429-2442, 1997;
Bratton, D. L., et al., *J. Biol. Chem.,* 272:26159-26165, 1997;
Bursch, W., et al., *Trends Pharmacol. Sci.,* 13:245-251, 1992;
Kockx M. M., et al., *Cardiovasc. Res.,* 45:736-746, 2000;
Mallat, Z., et al., *Circulation,* 96:424-428, 1997;
Martin, S., et al., *J. Exp. Med.,* 182:1545-1556, 1995;
Pugsley, W., et al., *Stroke,* 25:1393-1399, 1994;
Sims, P. J., et al., *Thromb. Haemost.,* 86:266-275, 2001;
Stary, H. C., et al., *Circulation,* 92:1355-1374, 1995;
Van den Eijnde, S. M., et al., *Cell Death Diff.,* 4:311-316, 1997.

The above references will be acknowledged in the text below by indicating in brackets, from the above list, the name of the first author and the year of publication.

BACKGROUND OF THE INVENTION

Biological membranes of intact eukaryotic cells are characterized by a highly organized structure. This high level of organization is determined, among others, by the molecular structure of the specific lipids constituting the membranes; the ratio between the various lipid species from which the membrane is composed; the distribution of the phospholipids between the outer and inner leaflets of the membranes; and by the protein components of the membrane.

While maintenance of the high level of membrane organization is fundamental to normal cell physiology, substantial perturbations and alterations of the normal organization of membrane (PNOM) occur in numerous physiological and pathological conditions, and are characterizing a plurality of diseases (Martin, S., et al., 1995). Such alterations and perturbations may be evident both at the morphological level (membrane blebbing observed in cells undergoing apoptosis) and at the molecular level. The scope of perturbations accompanying either cell activation, cell disease or cell death is not fully elucidated. They include, among others, scrambling and redistribution of the membrane phospholipids, with movement to the cell surface of aminophsopholipids, mainly phosphatidylserine (PS) and phosphatidylethanolamine (PE), which are normally restricted almost entirely to the inner leaflet of the membrane bilayer, and movement of sphingomyelin and phosphatidylcholine from the outer leaflet to the inner leaflet of the membrane (Sims, P. J., et al., 2001). This redistribution is referred herein as loss of cell membrane lipid asymmetry (CMLA). These alterations play an indispensable role in making the cell surface a catalytic platform for the assembly of several clotting factor complexes, such as tenase and prothrombinase complexes (Bevers, E. M., et al., 1999). Thus, platelets undergo PNOM upon activation, and these alterations constitute an important factor in normal blood coagulation, as well as in the initiation and/or propagation of abnormal, excessive blood clotting in numerous disorders. These disorders include, among others, arterial or venous thrombosis or thrombo-embolism [e.g., cerebral stroke, myocardial infarction, deep vein thrombosis (DVT), disseminated intravascular coagulation (DIC), thrombotic thrombocytopenic purpura, etc.]; unstable atherosclerotic plaques, sickle cell disease; beta-thalassemia; anti-phospholipid antibody syndrome; among others in systemic lupus erythematosus (SLE); disorders associated with shedding of membrane microparticles, e.g., neurological dysfunction in association with cardiopulmonary bypass.

Apoptosis is another major situation in which alterations/perturbations of cellular membranes take place (Bratton, D. L., et al., 1997). Apoptosis is an intrinsic program of cell self-destruction or "suicide", which is inherent in every eukaryotic cell. In response to a triggering stimulus, cells undergo a highly characteristic cascade of events of cell shrinkage, blebbing of cell membranes, chromatin condensation and fragmentation, culminating in cell conversion to clusters of membrane-bound particles (apoptotic bodies), which are thereafter engulfed by macrophages (Bursch, W., et al., 1992). PNOM is a universal phenomenon in apoptosis, it occurs early in the apoptotic cascade, probably at the point of cell commitment to the death process, and has also been shown to be an important factor in the recognition and removal of apoptotic cells by macrophages (Van den Eijnde, S. M., et al., 1997).

A strong correlation has been recently drawn between PNOM and potent procoagulant activity of apoptotic cells (Bombeli, T., et al., 1997). PNOM in apoptotic endothelial cells, such as in atherosclerotic plaques (Mallat, Z., et al., 1997), probably plays an important role in the pathogenesis of thrombotic vascular disorders. PNOM is also a feature of inflammatory cells (i.e., lymphocytes, macrophages), activated by various triggers.

Compounds for selective binding to PNOM membranes may therefore serve as an important tool for detection and targeting of cells undergoing activation, damage or death process, especially by apoptosis. In the clinical context, binding to said membranes may be useful in: (1). a diagnostic aspect (e.g., to diagnose disease processes, to monitor course and progression of disease, to monitor the effect of various therapeutic approaches on disease course); (2). a therapeutic aspect (e.g., drug targeting to PNOM cells, and/or modulation of PNOM-associated disorders); and (3). in a clearance aspect (selective binding and removal of PNOM elements from body fluids).

SUMMARY OF THE INVENTION

The present invention is based on the finding of compounds, which can selectively bind to cells undergoing perturbation of their normal organization of membrane (PNOM), while binding to a much lesser degree to cells which maintain the normal organization of their membrane.

The term PNOM for the purpose of the present invention refers to a cell membrane featuring at least one of the following:

(i) Scrambling of membrane phospholipids, with reduction of normal asymmetry of distribution of phospholipids between the inner and outer leaflets of the cell membrane;

(ii) Exposure of aminophospholipids on the outer cell surface (mainly exposure of phosphatidylserine and phosphatidylethanolamine);

(iii) Impairment of packing of membrane constituents;

(iv) Impairment of normal distribution of lipids within each membrane leaflet, such as formation of lateral domains, being either enriched or poor in a specific lipid membrane constituent, e.g., phosphatidylserine or cholesterol, respectively.

The term "perturbed membrane-binding compound" (PMBC) refers to a compound that binds selectively to membranes characterized by PNOM, while binding to a lesser degree to normal membranes.

The PMBC is used in the invention in the preparation of an agent that selectively binds to perturbed membranes. The PMBC group of compounds is designated "NST700". The PMBC group includes new compounds and also known compounds.

Thus, the present invention provides, according to one of its aspects, use of a perturbed membrane binding compound (PMBC) in the preparation of an agent for selectively binding to cells undergoing perturbation of their normal organization of membrane, said PMBC having the formula $C_e$, wherein e is selected among 1, 2 and 3 and C is a group having the formula (I):

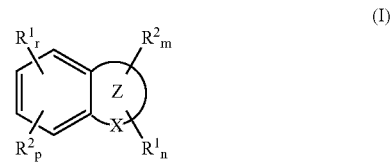

or pharmaceutically acceptable salts and hydrates of the structure of formula (I), wherein said C groups may each be the same or different and;

Z represents a ring system formed of cycloalkyl, cycloalkenyl, heterocyclyl, aryl or heteroaryl groups or combinations of such groups, said ring system consisting of 5-10 atoms;

X represents $CH$, $CH_2$, $N$, $NH$, $O$ or $S$;

n, m, r and p are each independently 0 or 1; wherein n+r=1; m+p=1;

$R^1$ groups may each be the same or different and are independently selected from the group consisting of A and L-A, wherein L groups may each be the same or different and are independently selected from the group consisting of D, U, U-D, D-U, D-U-O, O-U-D, D-U-NH, NH-U-D, D-U-D, and U-D-U;

U stands for a hydrogen or is selected from optionally substituted $C_1$-$C_6$ alkylene, $C_2$-$C_6$ alkenylene, $C_3$-$C_6$ branched alkylene, $C_3$-$C_6$ branched alkenylene, $C_3$-$C_6$ cycloalkylene, cycloalkenylene, aryl, heterocycloalkylene, heterocycloalkenylene, heteroaryl, and any combinations of said groups;

D is selected from the group consisting of $O$, $S$, $SO$, $SO_2$, $SO_2NH$, $NHSO_2$, $NH$, $PO$, $PO_2$, $POOH$, $PO(NH)_2$, $NHPOOH$, $CO$, $C(O)O$, $NHCO$, $CONH$, $SO_2NHCHCOOH$, $SO_2NHCO$ or the corresponding meaning from the above list when D is a bivalent radical;

A groups may each be the same or different and are charged moieties at pH of about 7 when e is 1; or when e is 2 or 3, A groups are independently selected from polar uncharged moieties and charged moieties at pH of about 7, said charged moieties being either positively-charged, negatively-charged or in zwitterion form.

$R^2$ is $WR^3_b$, where W is null or is selected from the group consisting of secondary or tertiary amine, oxygen, sulfur, carbon and D, wherein D is as defined above;

$R^3$ represents hydrogen or a $C_1$-$C_6$ alkyl, or $C_2$-$C_6$ alkenyl, $C_3$-$C_8$ branched alkyl, $C_3$-$C_8$ branched alkenyl; $R^3$ moieties may be either the same or different, b is 1, 2 or 3, and when e is 2 or 3, the C groups are linked to each other either directly or through an L moiety, wherein L is as defined above.

In a preferred embodiment e is 2.

In yet another preferred embodiment, the Z group of the PMBC of Formula I above represents a ring system formed of cycloalkyl, cycloalkenyl, heterocyclyl, aryl or heteroaryl, said ring system consisting of 5 or 6 atoms;

U stands for an optionally substituted $C_1$-$C_6$ alkylene, $C_2$-$C_6$ alkenylene, $C_3$-$C_6$ branched alkylene, $C_3$-$C_6$ branched alkenylene, and any combinations of said groups;

and $R^1$ consist of $WR^3_b$, wherein W is null or is selected from the group consisting of secondary or tertiary amine, oxygen and sulfur and $R^3$ and b are as defined above.

Preferably, b is 2, and $R^3$ groups are selected independently from the following combinations: (a) methyl groups (b) butyl groups; (c) hexyl groups; (d) a butyl and a methyl groups; (e) combination of an hexyl and a methyl groups;

In the PMBC of formula (I), each of $R^1$ and $R^2$ optionally may comprise a group Y, said Y group being a linker to any of the following:

1. Solid support;

2. Marker for imaging, e.g. detectors of fluorescence, x-ray, CT scan, magnetic resonance imaging (MRI), positron emission tomography (PET), or radio-isotope scan;

3. Another drug, being a medicinally-useful agent for the prevention or treatment of a specific disease, to be targeted to disease-inflicted cells or tissues via linkage to the PMBC. Preferably, the drug may be an inhibitor of apoptosis, (e.g., caspase inhibitor, antioxidant, modulator of the Bcl-2 system) or a cytotoxic agent, such as an activator of apoptosis (e.g., anticancer drugs); alternatively, the drug is preferably an anticoagulant, antithrombotic, or thrombolytic agent. In such case, said drug is preferably selected among an antiplatelet agent, heparin, low molecular weight heparin, antagonists of glycoprotein IIb/IIIa, tissue plasminogen activator (tPA), or an inhibitor of a clotting factor, such as an inhibitor of thrombin or an inhibitor of factor Xa; still alternatively, the drug is preferably an anti-inflammatory drug or an immuno-modulator drug.

Preferably, when e is an integer of 2 or 3, the C groups of the PMBC are linked to each other either directly or through an L moiety, wherein L is as defined above.

In another preferred embodiment, the PMBC used in the present invention comprises C groups having the following formula (II):

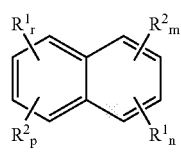

including pharmaceutically acceptable salts and hydrates of the structure of formula (II) wherein $R^1$, $R^2$, n, m, r and p all have the same meanings as defined above.

In another preferred embodiment, the PMBC of Formula (I) comprises C groups wherein said C groups consist of a naphthyl group (i.e., Z is a phenyl ring), one ring of such naphthyl is linked to a unit selected among the structures —$SO_2$—(NH)—$(CH_2)_v$-A, —$SO_2$—O—$(CH_2)_v$-A, wherein v stands for an integer of 1-5; the second ring of the naphthyl is linked to a monoalkyl or dialkyl amino group; and A is a charged group formed from amino group(s), and/or acidic group(s) such as carboxylic, phosphoric, phosphatic, sulfonic or sulfuric acid;

Preferably $R^3$ groups are selected among the following combinations: (a) two methyl groups; (b) two butyl groups; (c) two hexyl groups; (d) combination of a butyl and methyl groups; (e) combination of hexyl and methyl groups.

According to another preferred embodiment, the PMBC used in the present invention has C groups of the following Formula (III),

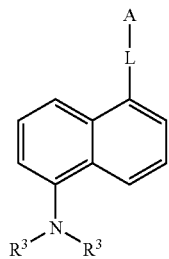

including pharmaceutically acceptable salts and hydrates thereof,
wherein A is a charged group formed from amino group(s) and/or carboxylic group(s) at least one of $R^3$ groups is $C_1$-$C_6$ alkyl group; and L is a —$SO_2$—(NH)—$(CH_2)_v$ (v stands for an integer of 1-5).

More specifically, the PMBC has the following Formula (IV), and is designated NST701:

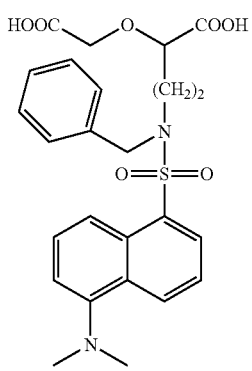

Some of the PMBCs are new compounds and represent a second aspect of the invention. These new compounds are of the structure $C_e$, wherein C is as defined above, and e is either 2 (i.e., the new compounds are dimers) or 1; wherein in the case that e=1, than the PMBC comprises an L group which is other than —$(CH_2)_5$—.

The following PMBCs are not new compounds:
N2,N6-bis[[5-(dimethylamino)-1-naphthalenyl]sulfonyl]-L-lysine, N,N'-bis[[5-(dimethylamino)-1-naphthalenyl]sulfonyl]-L-cystine, N,O-bis[[5-(dimethylamino)-1-naphthalenyl]sulfonyl]-L-tyrosine and N,N'''-bis[[2-(5-(dimethylamino) naphthalene-1-sulfonyl)aminoethyl] carbanioylmethyl]-diethylentriamine-N,N',N'''-triacetic acid.

Preferably the new compounds of the present invention have the following formula (V):

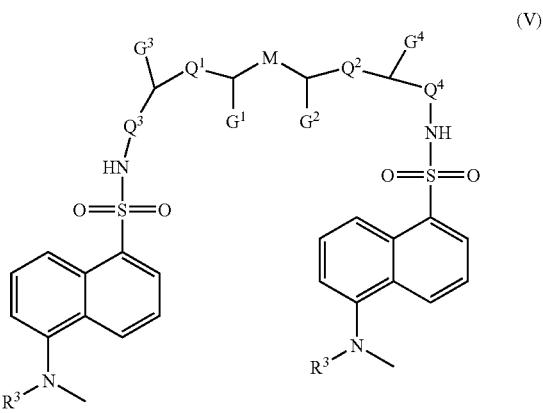

wherein $G^1$, $G^2$, $G^3$ and $G^4$ groups may be the same or different and are selected independently among hydrogen, COOH, C(O)$NH_2$, $NH_2$, and —N$(CH_3)_3$;

M is selected among null, NHC(O), C(O)NH, NH, O, S, S—S, $CH_2$, $(CH_2)_2$, NH—$(CH)_2$NH; N$(CH_2)_k$COOH, and $N^+(CH_3)(CH_2)_k$COOH;

$Q^1$, $Q^2$, $Q^3$ and $Q^4$ groups may be the same or different and are selected among null or $(CH_2)_k$, k being an integer of 1-6, and $R^3$ represents hydrogen or a $C_1$-$C_6$ alkyl. Preferably, $R^3$ is a methyl group, a butyl group or a hexyl group.

In a specific embodiment the new compound of the invention has the following formula (VI) and is designated NST740:

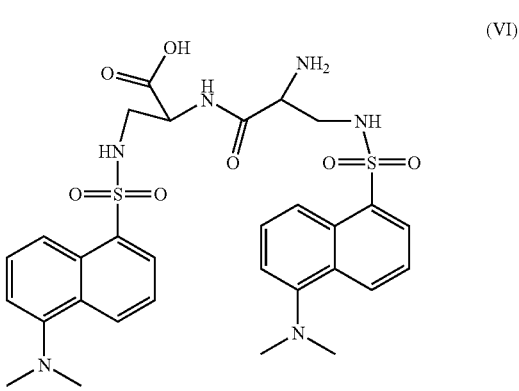

In another embodiment, new compounds of the invention have the following Formula (VII):

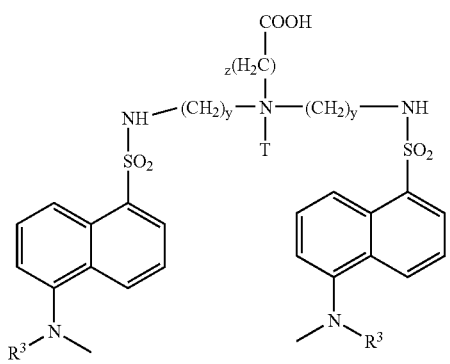

(VII)

including pharmaceutically acceptable salts and hydrates thereof,
wherein $R^3$ has the same meaning as defined above, y is an integer of 2-6, z is an integer of 1-6, and T is selected among null, hydrogen and methyl. Preferably, $R^3$ is selected among methyl, butyl or hexyl, y is 2 or 3, and z is 1, 2 or 3.

In yet another specific embodiment, the new compound of the invention has the following Formula (VIII), and is designated NST750:

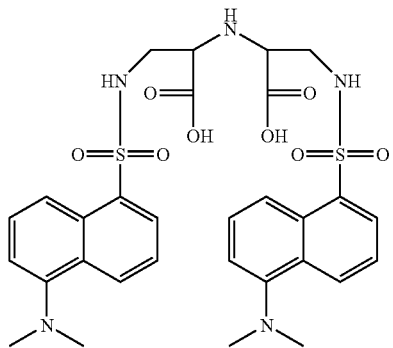

(VIII)

In another specific embodiment, the new compound of the invention has the following Formula (IX):

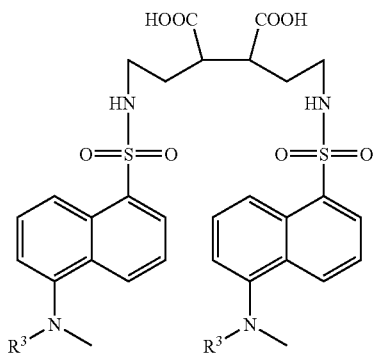

(IX)

including pharmaceutically acceptable salts and hydrates thereof,
wherein $R^3$ groups may be the same or different, and have the same meanings as above.

Preferably, the new compound has the structure of formula (IX) wherein $R^3$ is a methyl group and is designated NST751.

In a specific embodiment, the PMBC used in the present invention has the following Formula (X), and is designated DDL:

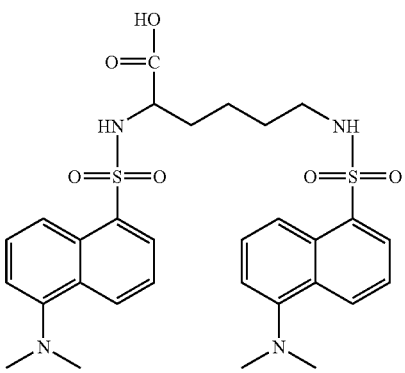

(X)

In another specific embodiment, the PMBC used in the present invention has the following Formula (XI), and is designated DDC:

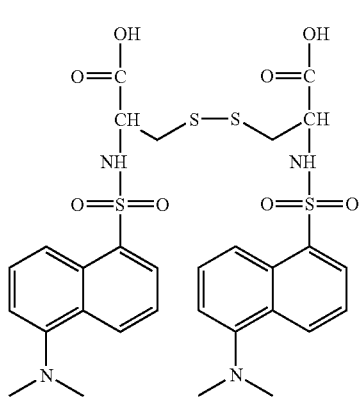

(XI)

In yet another preferred embodiment the PMBC used in the present invention has the following Formula (XII):

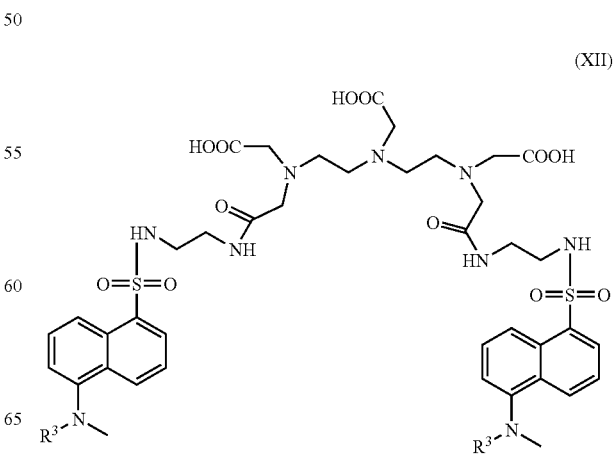

(XII)

including pharmaceutically acceptable salts and hydrates thereof, wherein $R^3$ is selected among a methyl group, butyl group and hexyl group.

The property of the PMBCs of selective binding to cellular membranes undergoing perturbation of normal organization (PNOM), while essentially not binding, or binding to a much lesser degree to membranes maintaining their normal organization, may be used in three different approaches of the invention.

According to a first approach, termed hereinafter the "detection approach" the selective binding may be utilized to detect cells, or cell-derived particles, which contain perturbed membranes (PM). This may be used for the diagnosis of diseases in which cells undergo PNOM as will be explained herein below.

According to a second approach, termed hereinafter the "therapeutic approach", the property of selective binding to PM may be utilized to treat diseases by using the PMBC as a targeting moiety, to target therapeutically useful drugs to organs and tissues in the body wherein PNOM occurs, e.g., regions of cell death, thrombus formation or inflammation.

In accordance with a third approach of the invention termed the "clearance approach", the selective binding of the compounds of the invention to PM, is utilized to clear body fluids from cells having PM, or of larger structures comprising such membranes, such as emboli circulating in the blood.

In accordance with the detection approach, the present invention concerns a composition comprising as an effective ingredient a PMBC as defined above, for the detection of a perturbed membrane in a sample of biological cells, either in vitro, ex vivo or in vivo. The PMBC in accordance with the detection approach of the present invention is capable of selectively binding to PM present in the assayed sample. Then, said binding may be identified by any means known in the art. The PMBC may have detectable properties of its own such as fluorescence emission, and these detectable properties may be detected, for example, by a fluorescent microscope, or by flow cytometric equipment.

The term "disease characterized by PM" refers to a disease which one of its manifestations is the perturbation of normal organization of membranes. This is not meant to read that this perturbation is necessarily the cause, or the sole effect of the disease, but rather that it is one of its manifestations.

In accordance with a preferred embodiment of the invention, the PMBC may comprise or may be bound, via a Y moiety, to a detectable label such as a fluorescence-emitting moiety, a radio-label, a label capable of undergoing an enzymatic reaction producing a detectable color, a marker for x-ray, MRI, radio-isotope imaging or PET scan, to produce a PMBC-label adduct. Such adduct enables the binding of the detectable label, through the compound of the invention, to PM in a selective manner. Then, the detectable label can be detected by any manner known in the art, and in accordance with the specific label used, for example, fluorescence, radio-active emission, or a color production, MRI, x-ray and the like. The term "bound" refers to covalent or non-covalent (e.g., electrostatic) binding, which connects the PMBC to the detectable label. Alternatively, the PMBC may have, because of the chemical nature of its structure, detectable properties of its own that enable it to be detected by any of the above mentioned techniques.

Preferably, said detectable label is selected among the metal ions Tc-99m and In-111 for radio-isotope scan, and Gd for MRI. Advantageously, Y comprises a metal chelator, said metal being a detectable label, wherein said chelator is selected among any of the following structures:

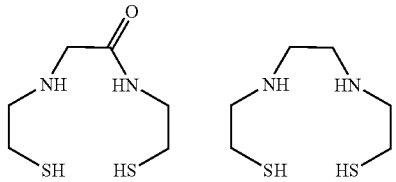

wherein the chelator being linked to the compound via one of its amino groups.

Still Advantageously, the Y linker comprises an L unit, linking the chelator to either the carboxyl, amine or sulfonamide moieties of the PMBC; said L unit being as defined above. The above adducts can be used for a detection and diagnosis of a wide variety of physiological conditions (including normal conditions), pathological conditions, diseases or disorders which are characterized by formation of PM.

Examples of conditions characterized by PM are as follows:

Diseases which are characterized by occurrence of excessive apoptosis, such as degenerative disorders, neurodegenerative disorders (e.g., Parkinson's disease, Alzheimer's disease, Huntington chorea), AIDS, myelodysplastic syndromes, ischemic or toxic insults, graft cell loss during transplant rejection; tumors, and especially highly malignant/aggressive tumors, are also often characterized by enhanced apoptosis, in addition to the excessive tissue proliferation.

Diseases manifested by excessive blood clotting, wherein PNOM occur during platelet activation, and/or during activation of or damage to other cellular elements (e.g., endothelial cells). These diseases include, among others, arterial or venous thrombosis, thrombo-embolism, e.g., myocardial infarction, cerebral stroke, deep vein thrombosis, disseminated intravascular coagulation (DIC), thrombotic thrombocytopenic purpura (TTP), sickle cell diseases, thalassemia, antiphospholipid antibody syndrome, systemic lupus erythematosus.

Inflammatory disorders, and/or diseases associated with immune-mediated etiology or pathogenesis, such as autoimmune disorders such as antiphospholipid antibody syndrome, systemic lupus erythematosus, connective tissue disorders such as rheumatoid arthritis, scleroderma; thyroiditis; dermatological disorders such as pemphigus or erythema nodosum; autoimmune hematological disorders; autoimmune neurological disorders such as myasthenia gravis; multiple sclerosis; inflammatory bowel disorders such as ulcerative colitis; vasculitis.

Atherosclerotic plaques, and especially plaques that are unstable, vulnerable and prone to rupture, are also characterized by PM structures, comprising apoptotic macrophages, apoptotic smooth muscle cells, apoptotic endothelial cells, activated platelets and activated inflammatory cells.

The detection of these pathological conditions, disorders or diseases via detection of the associated PNOM may be an aim by itself, simply for diagnosis of the presence of a disease condition in a specific individual.

Said detection may also be carried out in a person already known to have the disease for the purpose of evaluating the disease severity and in order to monitor response to various therapeutic modalities. An example for such monitoring is evaluation of response to anticancer therapy. Since most anti-tumor treatments, chemotherapy or radiotherapy exert their effect by induction of apoptosis, detection by PMBC of therapy-induced apoptotis of tumor cells may substantially shorten the lag period between the time of administration of an anti-cancer treatment and the time of proper evaluation of their efficacy.

Moreover, said detection may be used to monitor adverse effects of anti-cancer treatments. A large part of such adverse effects are due to untoward treatment-induced apoptosis in normal, yet sensitive cells, such as those of the gastrointestinal epithelium or the bone marrow hematopoietic system. Detection by the PMBC of such apoptosis may allow early detection of this untoward tissue damage and better optimization of the treatment protocol.

In addition, said detection may aim at characterization of intrinsic apoptotic load within a tumor, characterization of the level of aggressiveness of a tumor, and detection of metastases.

Similarly, the composition or the compounds of the current invention may be useful in monitoring graft survival after organ transplantation, since apoptosis, potentially detectable by PMBC compounds, plays a major role in cell loss during graft rejection.

In addition, said detection may aim at monitoring response to cyto-protective treatment and thus aid in screening and development of drugs which are capable of inhibiting cell loss in various diseases (for example those recited above) by enabling a measure of evaluation of cell death.

Said detection may be also useful for the detection of atherosclerotic plaques, since the destabilization of such plaques, rendering them vulnerable, prone to rupture, thrombosis and embolization, is characterized by participation of several elements, of which have in common perturbed membranes: (i). apoptotic cells: the unstable plaque is characterized by apoptotic macrophages, apoptotic smooth muscle cells, and apoptotic endothelial cells (ii). activated platelets (iii). activated inflammatory cells. A lipid core, comprising of extracellular accumulation of lipids is also one of the hallmarks of atheroscleorotic plaques undergoing destabilization (Kockx M. M., et al., 2000; Stary, H. C., et al., 1995). The PMBCs and compounds of the invention may be useful, due to their hydrophobic aromatic component, also for the identification of such lipid core of the vulnerable ahterosclerotic plaque.

The detection may also take place for basic research purposes in the study of apoptosis in tissue culture and animal models, and may also help in determining the role of apoptosis in normal development and homeostasis of various tissues, such as in the development of the central nervous system during embryogenesis, as well as during situations such as normal aging.

In accordance with this approach, the present invention further concerns a method for the detection of PM in biological cells, the method comprising:
  (i) contacting the cell sample with a PMBC under conditions enabling binding of said PMBC to biological membranes;
  (ii) detecting bound compound to said cells; the presence of a significant amount of bound compound indicating the presence of PM in said cells.

The method of the present invention may be used for the diagnosis of a disease characterized by the occurrence of PNOM, for example, any one of the diseases indicated above.

The method of the present invention may also be used for monitoring the effects of various therapeutic modalities for said diseases or medical conditions, or alternatively for basic science research purposes as explained above.

In accordance with a second approach of the invention, termed "the therapeutic approach", the present invention concerns a pharmaceutical composition comprising an active ingredient, optionally with a pharmaceutically acceptable carrier; said active ingredient comprising a PMBC-conjugate formed of (i) a pharmaceutically-active drug; and (ii) a PMBC. Said pharmaceutical composition acts to target the drug to cells undergoing PNOM, and can therefore be useful for the treatment of a disease characterized by the presence of PM as defined above.

The term "PAMC-conjugate" is used to denote a conjugate, comprising a drug associated with a complementary unit of a PMBC, wherein said conjugate being capable of acting as a PMBC. Said association may be by covalent binding, by non-covalent binding (e.g., electrostatic forces) or by formation of carrier particles (such as liposomes) comprising the drug having on their surface PMBC which targets the complex to the PM.

The purpose of a PMBC-conjugate is to direct the drug selectively only to cells, tissues or organs which feature PNOM, or which feature a significant amount of PNOM. Once the drug reaches the target it should be able to exert its physiological activity, either when still being in complex as part of the PMBC, after disconnecting from the complementary PMBC unit (for example by cleavage, destruction, etc., activity of natural enzymes), by phagocytosis of a drug-containing liposome having PMBC on its membrane, or by any other known mechanism.

The drug should be chosen in accordance with the specific disease for which the composition is intended.

For treatment or prevention of diseases which are manifested by initiation or propagation of abnormal and excessive blood clotting [e.g., arterial or venous thrombosis, thromboembolism, sickle cell diseases, beta-thalassemia, antiphospholipid antibody syndrome, disseminated intravascular coagulation (DIC), thrombotic thrombocytopenic purpura (TTP), systemic lupus erythematosus, the drug should be a compound which is known to inhibit formation of blood clots, or to dissolve blood clots after they have been produced, such as an antiplatelet agent, heparin, low molecular weight heparin, antagonists of glycoprotein IIB/IIIA, tissue plasminogen activator (tPA), or an inhibitor of a clotting factor, such as an inhibitor of thrombin, or an inhibitor of factor Xa.

Where the disease is manifested by inappropriate and excessive apoptosis such as degenerative disorders, neuodegenerative disorders (e.g., Parkinson's disease, Alzheimer's disease, Huntington chorea), AIDS, myelodysplastic syndromes, ischemic or toxic insults, graft cell loss during transplant rejection, the drug should be capable of inhibiting apoptosis. Such drug may be, among others, a caspase inhibitor, a modulator of the Bcl-2 system or an anti-oxidant.

Where disease is an Inflammatory disorder, and/or disease associated with immune-mediated etiology or pathogenesis, such as auto-immune disorders for example antiphospholipid antibody syndrome, systemic lupus erythematosus, connective tissue disorders such as rheumatoid arthritis, scleroderma; thyroiditis; dermatological disorders such as pemphigus or erythema nodosum; autoimmune hematological disorders; autoimmune neurological disorders such as myasthenia gravis; multiple sclerosis; inflammatory bowel disorders such as ulcerative colitis; vasculitis, the drug should be an anti-inflammatory drug, or an immuno-modulator drug.

For the treatment or prevention of unstable atherosclerotic plaque, characterized by thrombosis, inflammation or apoptosis, the drug can be chosen from the above groups of drugs.

The conjugate of the invention may comprise an anticancer drug in order to enhance the efficacy of anticancer protocols. The enhancement of an anti-cancer protocol is achieved by either: (1). Targeting of said conjugate to a tumor tissue, characterized by an abnormally excessive apoptotic load (the latter being often correlated to the level of tumor aggressiveness); or (2). Use of two waves of apoptosis: the first wave is achieved by using a standard chemotherapeutic or radiotherapeutic agent, aimed at initiating an apoptotic process within the tumor; followed by a second wave of apoptosis, in which the anticancer drug is administered as a PMBC-drug conjugate, being targeted to the apoptotic cells produced by the first wave. Thus, augmentation of the local concentrations of the anticancer drug within the tumor mass is achieved, with consequent enhancement of the local tumor-killing process.

The pharmaceutical composition of the invention may be administered by any of the known routes, inter alia, oral, intravenous, intraperitoneal, intramuscular, subcutaneous, sublingual, intraocular, intranasal or topical administration. The carrier should be selected in accordance with the desired mode of administration, and include any known components, e.g. solvents; emulgators, excipients, talc; flavors; colors, etc. The pharmaceutical composition may comprise, if desired, also other pharmaceutically-active compounds which are used to treat the disease, eliminate side effects or augment the activity of the active component.

The present invention also concerns use of a PMBC comprising a drug, i.e., a PMBC-conjugate for the preparation of a medicament.

The use in accordance with the present invention is preferably for the preparation of a medicament for the treatment and detection of diseases characterized by presence of PM, and/or in diseases in which PM has an etiological or a pathogenetic role. Examples of such diseases are given above.

The present invention in accordance with this aspect, still further concerns a method for improvement of treatment of a disease manifested by PM, comprising administering to an individual in need of such treatment an effective amount of a PMBC-conjugate, said conjugate comprising a drug being active as a treatment for said disease. The conjugate allows for selective targeting of the drug to the PNOM-inflicted tissues, thus augmenting its local concentration, and potentially enhancing its therapeutic effect at the target site. Such medical disorders are those defined above.

The term "effective amount" refers to an amount capable of decreasing, to a measurable effect, at least one adverse manifestation of the disease and should be chosen in accordance with the drug used, the mode of administration, the age and weight of the patient, the severity of the disease, etc.

By a third approach, termed the "clearance approach", the properties of the PMBCs to bind specifically to PM are utilized to clear body fluid of cells, particles, microparticles or any structures containing PM. Preferably, the body fluid is blood or a blood product.

Many surgical or medical interventions requiring extracorporeal circulation are associated with an exposure of blood elements to exogenous artificial environment. This often leads to activation of and damage to blood cells, systemic inflammation, and thromboembolic phenomena, potentially having serious clinical consequences, such as neurological dysfunction. It is therefore desirable to detect and remove said damaged, activated or apoptotic blood cells.

Thus, the present invention concerns a PMBC immobilized on a solid support. Said immobilization may be by direct attachment, either by covalent or non-covalent binding, or by attachment through a spacer. The immobilized PMBC is intended to clear a body fluid from PM cells or PM containing structures.

The term "PM cells" concerns cells which membranes undergo PNOM. Typically for blood or blood products, this includes activated, apoptotic or damaged red blood cells, white blood cells, platelets, platelet-derived microparticals, tissue macrophages and endothelial cells.

The term "PM-containing stucture" refers to an aggregation of cellular and/or non-cellular components, which contains membranes with PNOM. This term typically refers to microemboli, which are procoagulant particles and procoagulant cells. Said microemboli comprise activated platelets, platelet-derived microparticles, platelet-fibrin clots, damaged cells, senescent cells, apoptotic endothelial and blood cells, apoptotic bodies and cell debris. These elements are characterized by PM, and said microemboli may lodge in small distal blood vessels, occlude them and/or initiate local thrombosis, thus causing local ischemia. Indeed, is the widespread lodging of these microemboli in the capillaries of various organs, notably in the central nervous system, is currently considered a cardinal factor in the pathogenesis of organ damage and dysfunction following cardiopulmonary bypass during heart surgery (Pugsley, W., et al., 1994).

The term "solid support" refers in the contents of the present invention to a solid matrix, an insoluble matrix, and an insoluble support. The solid support in accordance with the present invention may be formed in a variety of structures such as a stack of micro-particulates, micro-filters, or micro capillara, and may be composed of various materials such as alumina, diatomaceous earth, celite, calcium carbonate, calcium sulfate, ion-exchange resin, silica gel, charcoal, amberlite, dowex, Eupergit and ethylsofoxycellulose.

According to preferred embodiments of the present invention, the solid support features a plurality of beads to which the PMBC are bound. Preferably, the beads are resin-coated beads. Alternatively, the beads may be magnetic beads.

Where the solid support includes a plurality of fibers or microcapillara, among and/or through which the body fluid flows, the inner and/or outer faces thereof are covered with the PMBC.

The compounds immobilized on a solid support form part of a filter device. Thus in accordance with the clearance approach, the present invention further concerns a filter device comprising a housing containing the PMBC immobilized on said solid support, and a fluid inlet and fluid outlet. Body fluids such as blood or blood products enter the housing through said inlet, come into contact and adhere to the immobilized PMBC contained in the housing. Thus, the body fluid is cleared of circulating cells having perturbed membranes, such as damaged or dying cells, or cleared of larger structures such as emboli having perturbed membranes. Consequently, fluid exiting from said outlet has a reduced content of said PM-containing cells or PM-containing structures or is essentially devoid of same.

The filter device may form a replaceable, a permanent, or an add-on portion of an extracorporeal circulation apparatus. Thus the present invention also concerns an extracorporeal circulation apparatus comprising said filter device, wherein blood circulating through the apparatus also passes through the device.

Examples of such apparatuses are cardiopulmonary bypass apparatus; hemodialysis apparatus; plasmapheresis apparatus and blood transfusion apparatus, such as state of the art blood transfusion bags.

The clearance aspect also provides a method for removal of PM-containing cells or PM-containing structures from a biological fluid, preferably a body fluid. The method comprising: contacting the body fluid with PMBC immobilized on a solid support, under conditions and for a time period sufficient for binding of PM-containing cells or PM-containing structures to the PMBC, thereby removing at least a portion of said PM-containing cells or particles from the body fluid.

The contact of the body fluid (such as blood or blood derived product) with the immobilized PMBC may be carried-out by any method known in the art to remove particles from fluid, and in particular by flowing the body fluid through the filter device of the invention, thereby clearing the blood from at least a portion of the microemboli present therein.

The method of the invention may be used to improve the clinical outcome of procedures involving extracorporeal circulation, such as surgery requiring cardiopulmonary bypass, thereby reducing the risk for thromboembolic events during the procedure, by removal of the potentially harmful PM-containing cells or PM-containing structures (notably microemboli) from blood. In practice, the filter device may be placed on the line leading from the extracorporeal circulation machine to the patient, thus performing filtration of PM cells or aggregates out of the blood. Alternatively, blood can be temporarily diverted to a system comprising the filter device for performance of the filtration of the PM elements, with return of the purified blood to the systemic circulation thereafter. The method may also be used to clear PM-containing cells or PM-containing structures from the circulation of a patient undergoing hemodialysis, or a patient undergoing plasmapheresis.

The method may also be used to treat stored blood prior to transfusion, so as to minimize the amount of PM-containing cells or PM-containing structures present therein and thus minimize various complications associated with transfusion of blood. For the treatment of stored blood, said filtration method may be used as part of the processing of blood in the blood bank, or during transfusion to the patient, in which case said filter may be placed on the line leading from the transfusion bag to the patient.

BRIEF DESCRIPTION OF THE DRAWINGS

In order to understand the invention and to see how it may be carried-out in practice, a preferred embodiment will now be described, in which detection of binding of the compounds of the present invention to cells undergoing PNOM, either due to apoptosis or due to activation, was evaluated. Binding was measured by monitoring of the intensity of the intrinsic fluorescence of the compounds, either by fluorescent microscopy or by flow cytometric (FACS) analysis. Said preferred embodiment will now be described by way of non-limiting example only, with reference to the accompanying drawings, in which.

DETAILED EXPLANATION OF FIGURES

Figure 1:
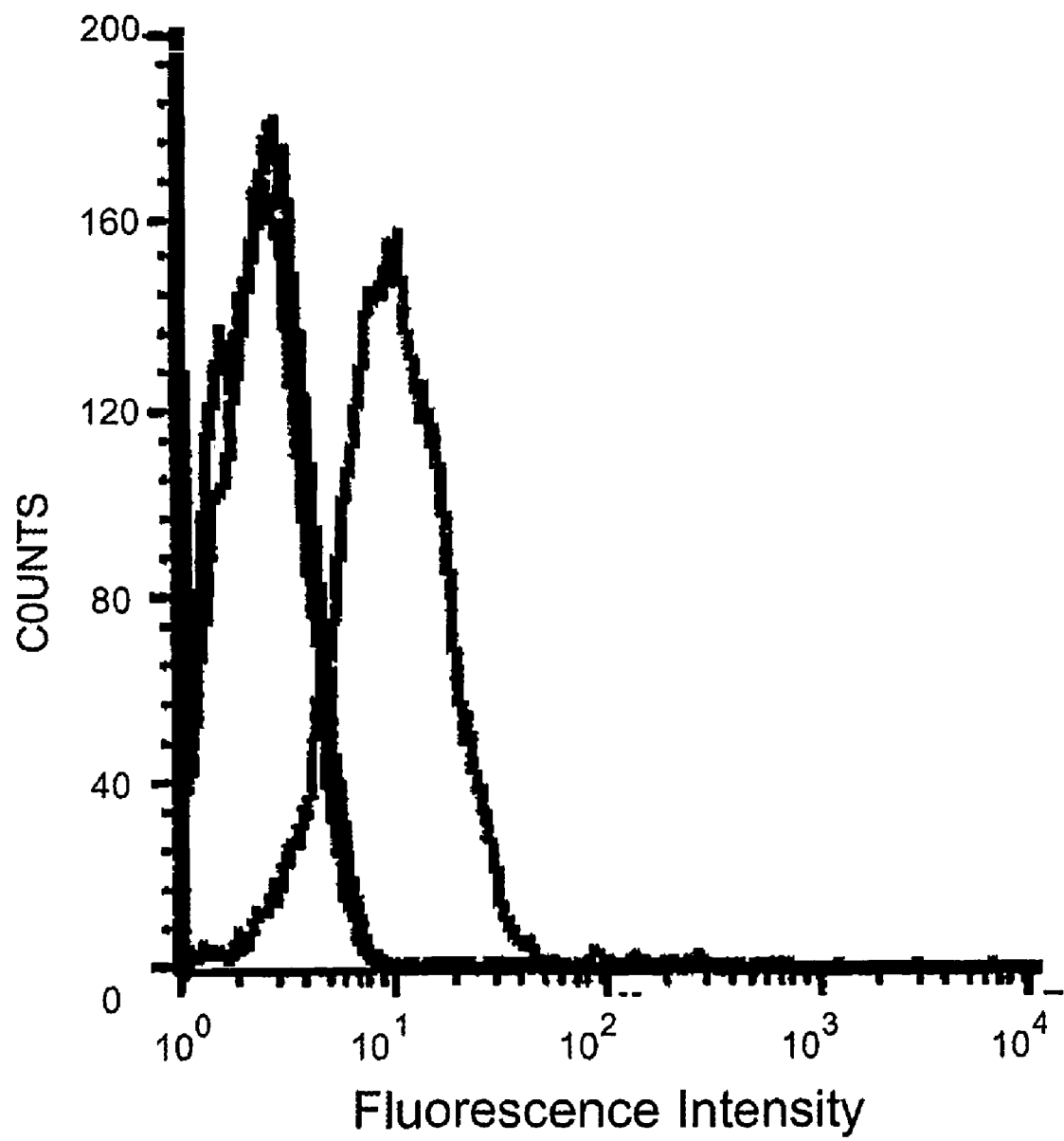
FIG. 1: Selective binding of DDL to activated red blood cells (RBC): flow cytometric analysis.

FIG. 1: Selective Binding of DDL to Activated Red Blood Cells (RBC): Flow Cytometric Analysis RBC were activated by treatment with N-ethylmaleimide (NEM) and calcium ionophore A23187, in the presence of $Ca^{2+}$ (Kuypers A. et al., 1996, Blood, 87, 1179-1187). DDL (final concentration of 1 μM) was added to activated and control, non-treated RBC. Cells were then subjected to flow cytometric (FACS) analysis, using Beckton-Dickinson cell sorter, and the CellQuest software. Excitation was at 360 nm and emission was at 530 nm. While intact RBC did not manifest significant binding of DDL [blue line, similar to the basal, background fluorescence, (black line)], activated RBC manifested significant DDC binding, reflected by a significant shift of the peak to higher fluorescence values (red line). X axis represents the fluorescence in 530 nm, and Y axis represents the number of counted RBC.

FIG. 2: Fluorescent Microscopy Showing the Selective Binding of DDC to Apoptotic Cells HeLa cells were induced to undergo apoptosis by exposure to 500 μM dopamine for 18 hours, and then incubated with DDC (100 μM). Non-treated cells served as control. Cell visualization was performed using by an IX70 fluorescent microscope (Olympus), measuring the intensity of the inherent fluorescence of the DDC compound (excitation wavelength of 360 nm, emission at 530 nm). In the control culture (a), intact cells remained un-stained. By contrast, in the apoptotic culture (b), most of the cells specifically bound DDC. The small fraction of cells within the control culture that bound DDC represents the naturally occurring process of cell death, typical for cells grown in culture (magnification is ×400).

Figure 3:
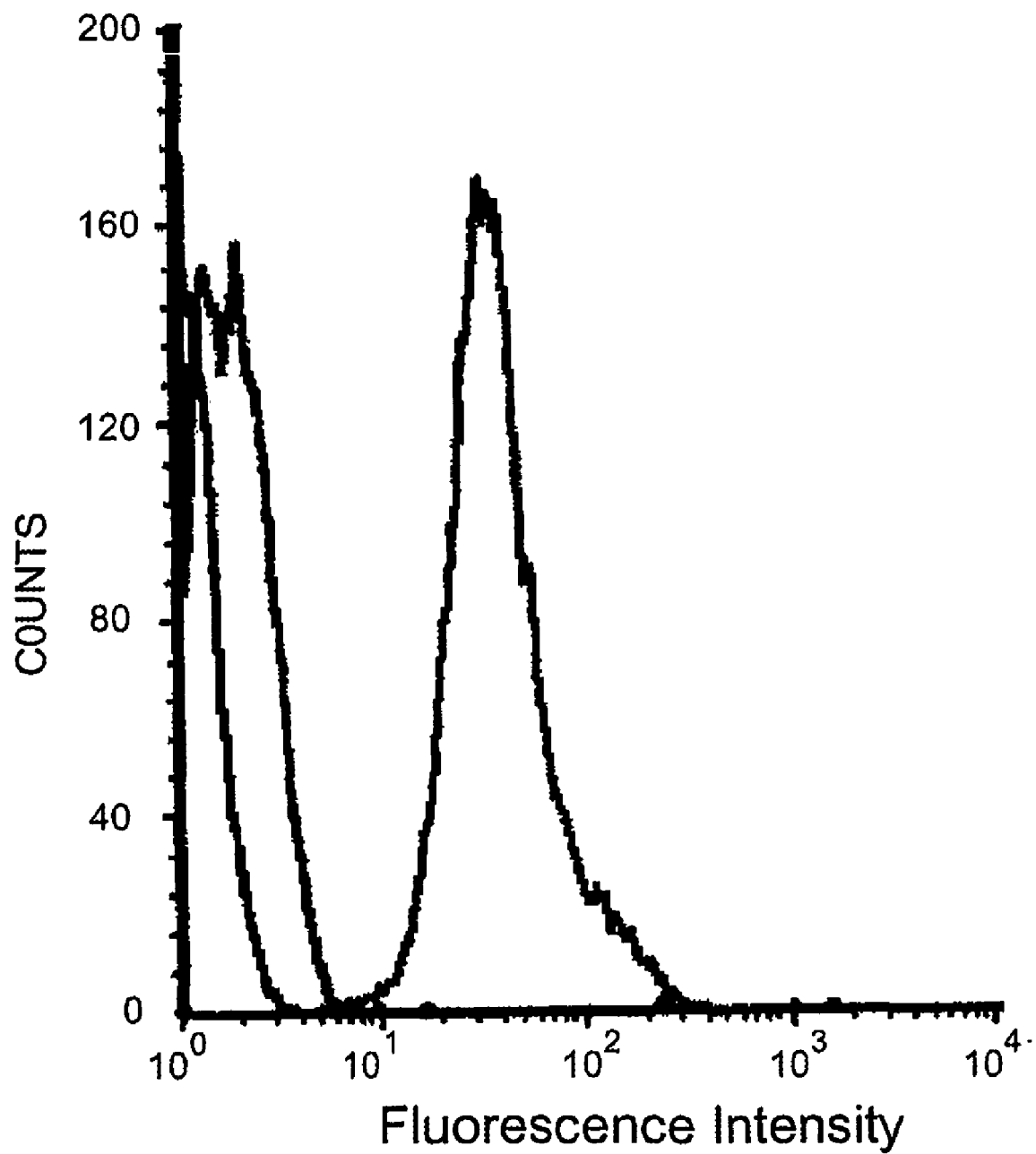
FIG. 3: Selective binding of DDC to activated red blood cells (RBC); flow-cytometric analysis.

FIG. 3: Selective Binding of DDC to Activated RBC; Flow-Cytometric Analysis:

DDC (final concentration of 500 μM) was added to control and activated RBC, and the cells were subjected to FACS analysis, using a Becton-Dickinson cell sorter and a CellQuest software. Excitation was at 360 nm and emission was at 530 nm. While intact RBC (black line) did not manifest a significant shift to higher fluorescence values upon addition of DDC (blue line), activated RBC were characterized by significantly higher DDC binding, as reflected by shifting of the peak to higher fluorescence values (red line). The X axis represents the fluorescence in 530 nm, and the Y axis represents the number of RBC.

Figure 4A:
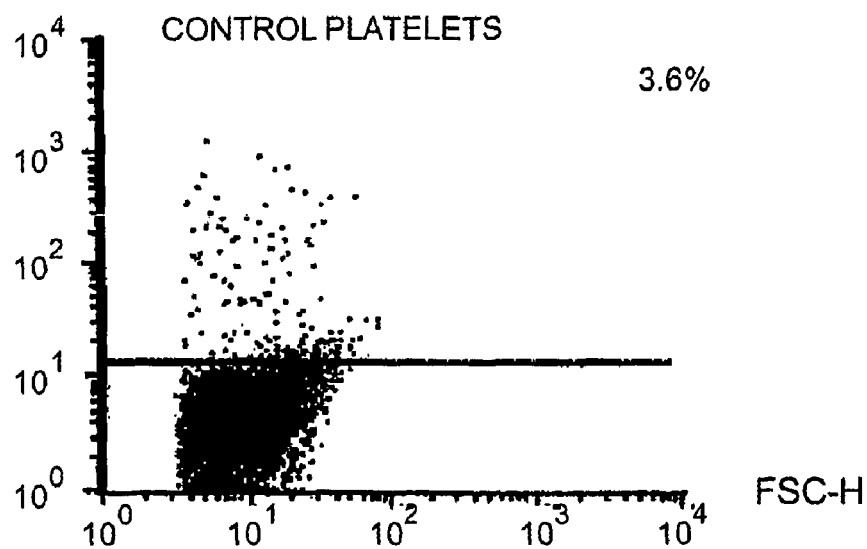
FIG. 4: Selective binding of DDC to activated platelets; flow-cytometric analysis.
Figure 4B:
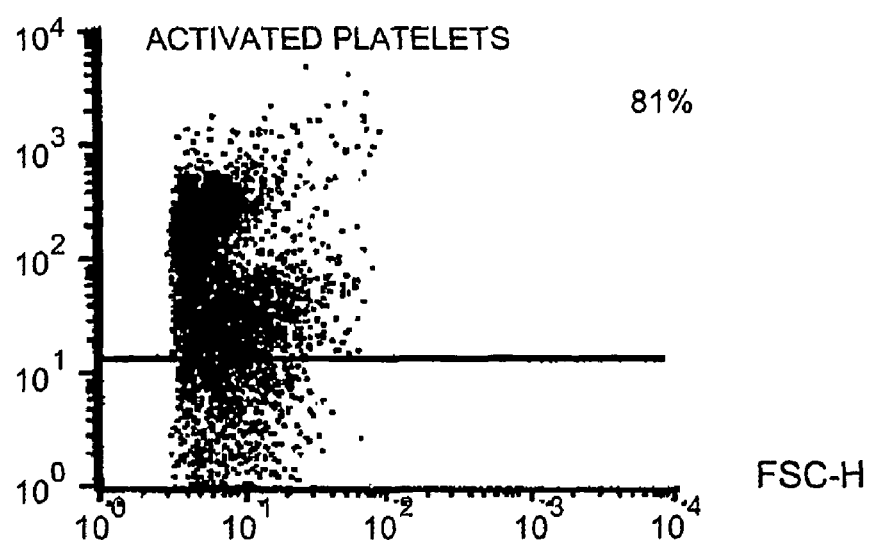
Figure 4C:
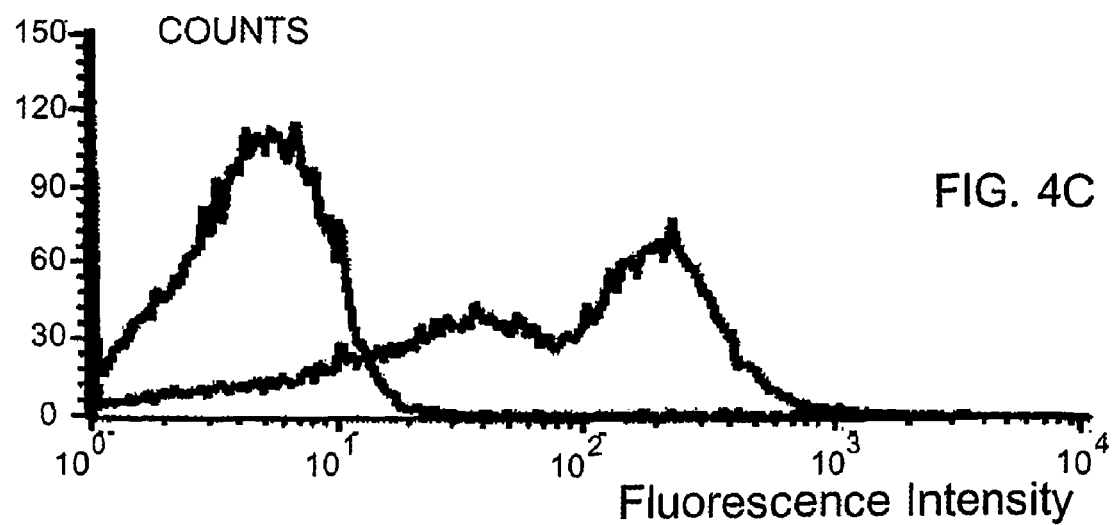

FIG. 4: Selective Binding of DDC to Activated Platelets; Flow-Cytometric Analysis Platelets were activated by exposure to collagen and thrombin. (a) shows FACS dot plot analysis of the selective binding of DDC to the activated platelets: Y-axis shows the fluorescence intensity at 530 nm, indicative of DDC binding, while the X-axis shows the forward-angle light scatter, which relates to cell diameter. Control platelets, shown in the left panel, manifested low levels of fluorescence, indicative of lack of significant binding of DDC. By contrast, platelets activated with collagen and thrombin (shown in the right panel) exhibited a markedly increased fluorescence values, indicative of a large fraction of platelets now being labeled with DDC. The numbers in the top rectangular of each panel designate the percentage of platelets within the population showing increased fluorescent values. (b) shows FACS histogram of the results: the X-axis shows fluorescence intensity at 530 nm; and the Y-axis shows the number of events; the black line represents fluorescence of control platelets, not treated with DDC, while the red line represents the DDC-stained, activated platelets. Upon activation, the peak of control platelets shows a strong shift towards higher fluorescence values, reflecting a marked selective binding of DDC to these cells.

FIG. 5: Detection of Liver-Cell Apoptosis In Vivo with DDC

Liver cell apoptosis was induced in mice by intravenous administration of anti-Fas Ab, according to the model by Ogasawara et al. (*Nature*, 364:806-809, 1993). DDC (70 mg/kg) was then injected to both anti-Fas-Ab-treated and control untreated animals. After two hours, animals were sacrificed, and the liver was removed and frozen. Cryo-sections were then prepared for histopathological analysis, which was performed using fluorescent microscopy (magnification X 600). (a) Control liver, (b) Liver treated with anti-Fas-Ab. Arrows point at hepatocytes undergoing apoptosis.

Figure 6A:
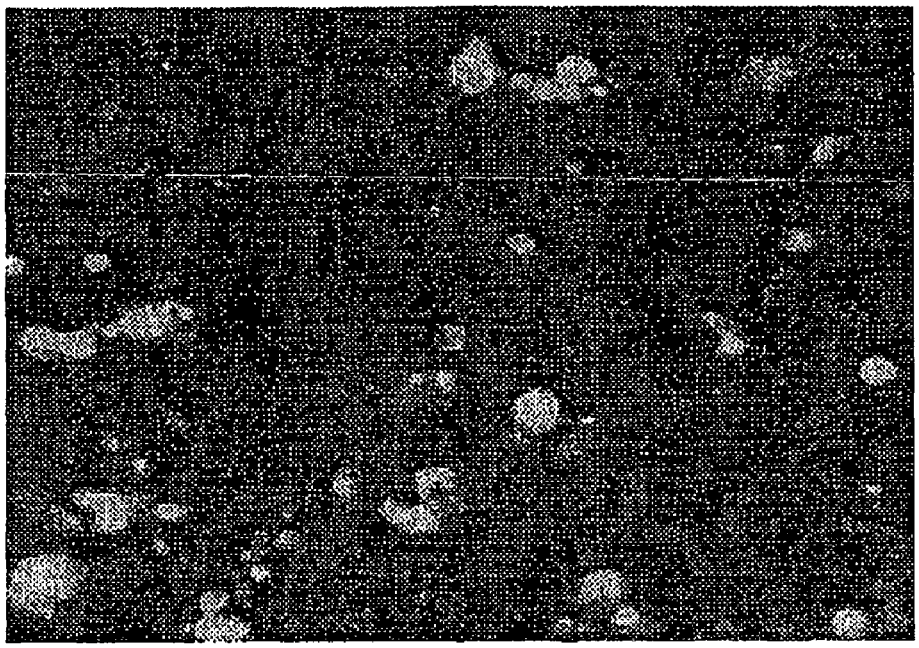
FIG. 6: Detection of apoptotic cells iii vivo within a tumor by DDC, correlation with TUNEL ex-vivo assay.
Figure 6B:
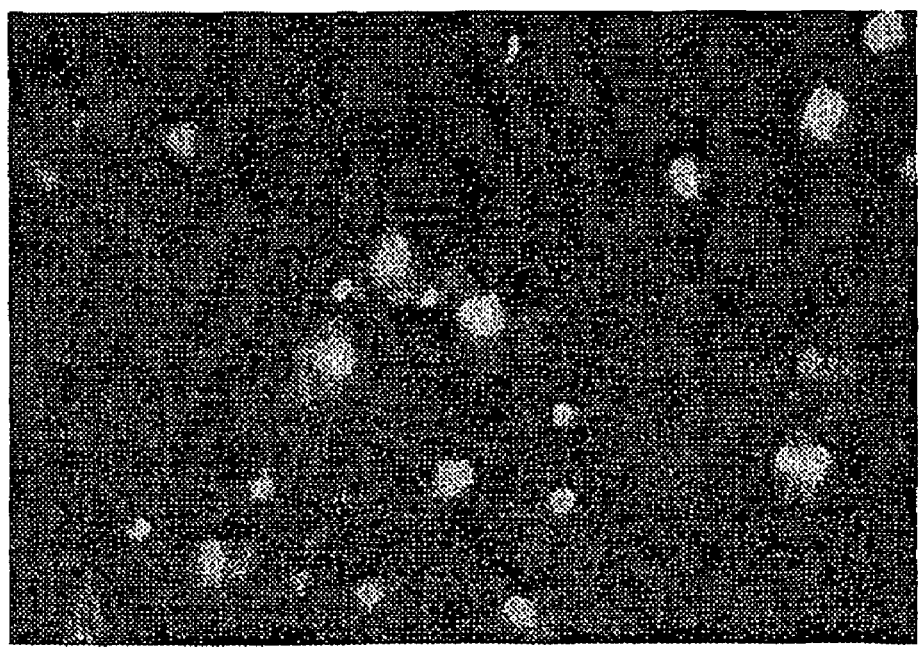

FIG. 6: Detection of Apoptotic Cells In Vivo within a Tumor by DDC, Correlation with TUNEL Ex-Vivo Assay D122 (small cell lung carcinoma) cells were injected subcutaneously to c57 black mice. After development of 2-3 mm tumors, DDC (70 mg/kg) was administered intravenously. Two hours later, tumors were dissected and frozen. Cryo-sections were then prepared for histopathological analysis, using fluorescent microscopy (magnification ×600). Single apoptotic cells are visualized as blue-green fluorescent cells—FIG. 6A. In order to demonstrate a correlation between binding of DDC to the cells and the apoptotic process, cryo-sections were also prepared for apoptosis evaluation ex-vivo, using the terminal deoxynucleotidyl-transferase (TdT)-mediated dUTP-biotin nick end-labeling (TUNEL) staining, which is a widely-accepted method for detection of the characteristic apoptotic DNA cleavage. Specific binding of DDC to cells undergoing apoptosis within the tumor was observed, in correlation with the TUNEL staining—FIG. 6B.

FIG. 7: Detection of Chemotherapy-Induced Apoptosis of Small Intestine Epithelial Cells In Vivo by NST750

Balb/c mice were treated with a single dose of a combination of Taxol (300 mg/kg) and cyclophosphamide (27 mg/kg). 24 hours later, the animals were injected intravenously with 13 mg/ml of NST750. Animals were sacrificed two hours later, and the small intestine tissue was subjected to fluorescent 15 histopathological analysis. Single apoptotic epithelial cells, detected by NST750, were observed in the crypts of the small intestine of the chemotherapy-treated mice (A), but not in the tissues from mice without chemotherapy (B).

EXAMPLES

Example 1

Selective Binding of DDL to Activated Red Blood Cells (RBC)

Selective binding of DDL to, activated/damaged RBC was demonstrated by activation of fresh RBC by a combined treatment with N-ethylmaleimide (NEM) and calcium ionophore A23187, in the presence of $Ca^{2+}$ (Kuypers A. et al., 1996; Blood, 87: 1179-1187). Binding of DDL was measured through detection of the intensity of its inherent fluorescence upon membrane binding (excitation wavelength of 360 nm, emission at 530 nm).

Fresh packed red blood were diluted to 0.1 of their initial volume with buffer A (143 mM NaCl; 2 mM KCl; 0.1% Glucose; 10 mM $NaH_2PO_4$; Ph=7.4), and washed 4 times in the above buffer. The cells were then re-suspended in buffer B (55 mM NaCl; 90 mM KCl; 0.1% glucose; 10 mM hepes; Ph=7.4). Cells prepared as above were used as control intact red blood cells. For activation, cells were treated with a combination of 2 mM CaCl; 5 µM of the calcium ionophore A23187 and 5 mm of NEM. Incubation was for 15-60 min at 370° C. Cells were then washed twice with buffer B containing 0.1% of BSA and re-suspended finally in Buffer B containing 2 µM $CaCl_2$. DDL was added at a final concentration of 1 µM, and evaluation of bound DDL was performed by FACS analysis.

As shown in FIG. 1, control RBC did not bind DDL significantly. By contrast, activated RBC manifested marked binding of DDL, with actually most cells shifting to higher fluorescence values (FIG. 1).

DDL therefore manifests selective binding to PNOM-inflicted RBC, induced, in this example, by cell activation.

Example 2

Selective Binding of DDC to Apoptotic Cells

HeLa S3 cells (ATCC CCL-2.2) were grown in Dulbecco's modified Eagle's medium (DMEM), supplemented with 2 mM of L-glutamine, 100 units/ml of penicillin, 100 µg/ml of streptomycin, 12.5 units/ml of nystatin and 10% of fetal calf serum (FCS). Cells were seeded at a density of $5 \times 10^6$ cells/plate on 10 $cm^3$ culture plates in a volume of 10 ml, and were cultured for 24 hours prior to induction of apoptosis.

Apoptosis was induced by treatment with dopamine (500 µM), which is a 5 well-substantiated trigger of apoptosis ((Lou J, et al., J Biol Chem 1998; 273:3756-3764) in the presence of a low serum-containing medium (2% FCS) for 18 hours. Non-treated cells that served as control were kept in the growing medium without dopamine. Following treatment, cells were harvested using a cell scraper, separated to single cells by passage through a syringe with a 18 G needle, and re-suspended at a density of $10^6$ cells/ml in PBS buffer at pH=7.4.

Cultures were grown as specified above, and washed twice with HBS (HEPES Buffered Saline; 10 mM HEPES; 150 mM NaCl; pH=7.4). Binding of DDC was measured through detection of the intensity of the inherent fluorescence of the compound upon membrane binding (excitation wavelength of 360 nm, emission at 530 nm). For said measurement of binding, cells were washed twice with TBS (Tris buffered saline; 10 mM Tris, pH 7.4, 150 mM NaCl). DDC was suspended in 0.1M NaPPi pH=7.4 at a concentration of 1 mM, and cells were then incubated with DDC at a final concentration of 100 µM for 2-10 minutes, in a total volume of 50 µL. Cells were then taken for fluorescent microscopy. Observations were preformed using an Olympus fluorescent microscope (model IX70, excitation wavelengths of 360 nm, emission at 530 nm).

Figure 2A:
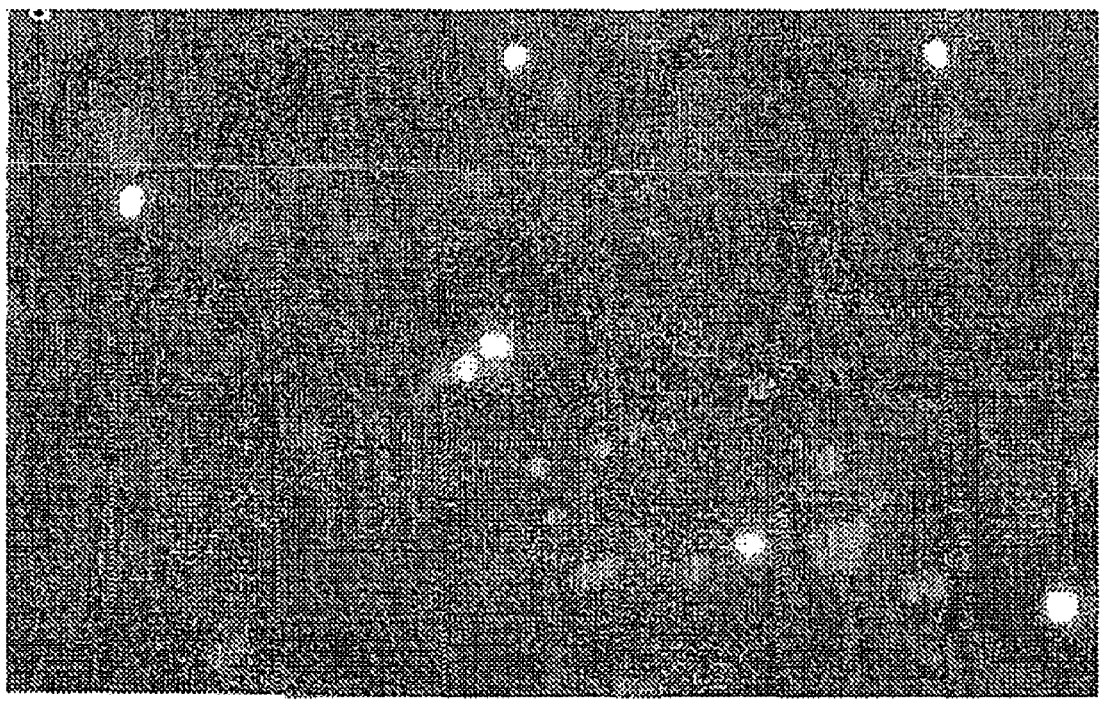
FIG. 2: Fluorescent microscopy showing the selective binding of DDC to apoptotic cells.
Figure 2B:
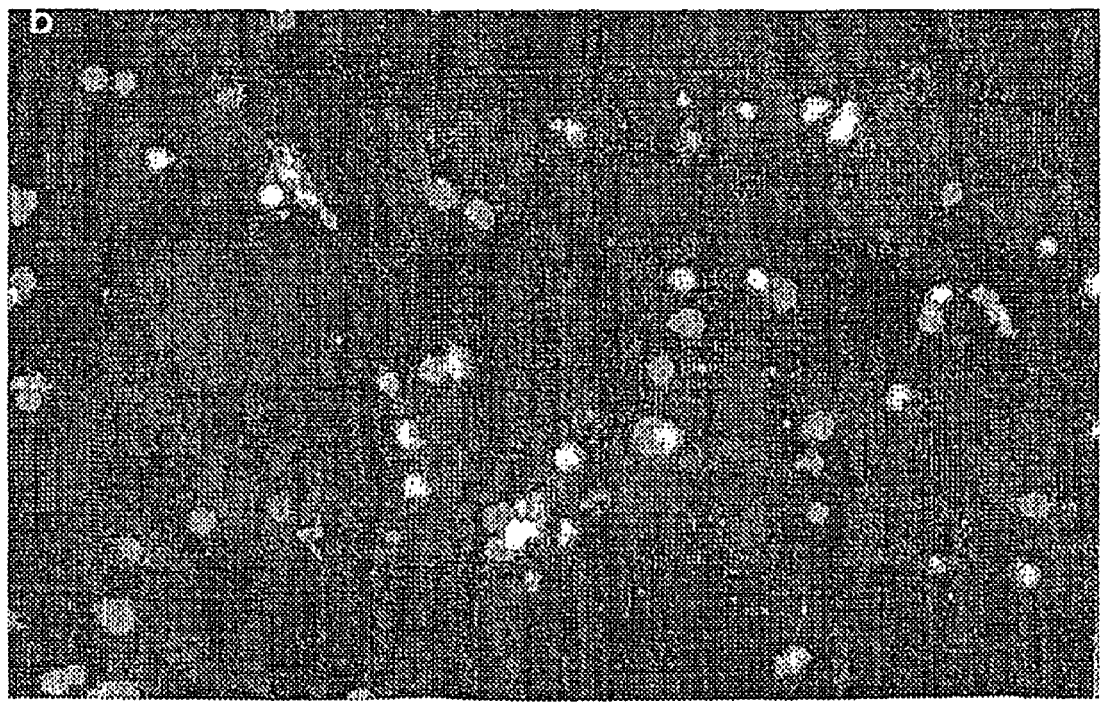

Strong fluorescence of single apoptotic cells was detected in the cultures of HeLa cells treated with the apoptotic trigger (FIG. 2B). The fraction of these cells, stained with DDC within the apoptotic cultures was high. By contrast, cultures of non-treated HeLa cells exhibited a very low fraction of stained cells, reflecting a naturally-occurring process of cell death within the culture (FIG. 2A). DDC, through its selective binding to PNOM membranes, therefore manifests selective binding to cells undergoing apoptosis in culture.

Example 3

Selective Binding of DDC to Activated Red Blood Cells (RBC); Low-Cytometric Analysis The selective binding of DDC to activated or damaged cells red blood cells (RBC) and to control, healthy RBC was explored and demonstrated. Activation of intact RBC, was induced by a combined treatment with NV-ethylmaleimide (NEM) and calcium ionophore, in the presence of $Ca^{2+}$ (Kuypers A. et al., 1996, Blood, 87:1179-1187).

Fresh RBC were obtained, diluted to 0.1 of their initial volume with buffer A (143 mM NaCl; 2 mM KCl; 0.1% Glucose; 10 mM $NaH_2PO_4$; Ph=7.4), and washed 4 times in the above buffer. Cells were then re-suspended in buffer B (55 mM NaCl; 90 mM KCl; 0.1% glucose; 10 mM HEPES; pH=7.4). These cells were thereafter used as control cells. For activation, the cells were treated for 15-60 min at 37° C. with a combination of 2 mM CaCl, 5 M of the Calcium ionophore A23187 and 5 mm of NEM. Cells were then washed twice with buffer B containing 0.1% of bovine serum albumin, and finally re-suspended in Buffer B containing 2 mM $CaCl_2$. For examination of binding of DDC to the cells, DDC was dissolved in 0.1M NaPPi, pH=7.4, at a stock concentration of 1 mM. Binding assays were performed at a final concentration of 500 µM, and level of binding was evaluated by flow cytometry.

As shown in FIG. 3, intact red blood cells did not stain significantly with DDC. However, as a result of RBC activation, the whole population of cells underwent a substantial shift to higher fluorescence levels, reflecting DDC binding. Therefore, DDC manifests selective binding to activated/damaged RBC.

Example 4

Selective Binding of DDC to Activated Platelets

The selective binding of DDC to activated platelets was determined using flow cytometric (FACS) analysis.

Platelet-rich plasma was obtained from healthy volunteers. $10^9$ of the fresh platelets were centrifuged (5 minutes, 380×g), washed and re-suspended in Tyrode's buffer (137 mM NaCl; 20.8 nM KCl; 1 mM $MgCl_2$, 12 mM $NaHCO_3$; 0.4 mM $NaBHPO_4$; 5.5 mM D-glucose and 10 mM Hepes pH 7.4; 0.35% BSA). The purified platelets were kept on ice, and served as controls.

For activation. 200 μl of washed platelets were incubated with a mixture of 0.05 units/ml of thrombin and 5 μg/ml collagen for 5 min. at 370, in the presence of 2 mM $CaCl_2$ in a final volume of 1 ml. Following incubation, the platelets were centrifuged (2 min. at 10 rpm) and resuspended in 1 ml of Tyrode's buffer.

Activated and control non-treated platelets were incubated with 10 μM of DDC for 5 minutes at room temperature. The platelets were then subjected to analysis by flow cytometry (SACS) using Beckton-Dickinson cell sorter and CellQuest software. Excitation was at 360 nm and emission was measured at 530 nm. FIG. 4A. Shows the fraction of platelets binding DDC upon activation. While only a small fraction of the control platelets manifested binding of DDC (3.6% of the population), platelet activation caused 81% of the platelet population to acquire a marked DDC binding, reflected as a distinct shift to higher fluorescence intensity. As shown in the FACS histogram in FIG. 4B, activation was associated with a major shift of the whole platelet population to higher fluorescence intensity. DDC can therefore act, through its detection of PNOM, as a potent agent to mark and distinguish between activated and non-activated platelets.

Example 5

Selective Binding of DDC to Apoptotic Cells In Vivo

Selective detection of apoptotic cells in vivo has numerous diagnostic and therapeutic clinical applications. In order to demonstrate the potential of DDC in performing this task, a well-characterized model of hepatic apoptosis in vivo, induced by intravenous administration of anti-Fas antibody was utilized (Ogasawara, J., et. al., *Nature* 364: 806-809, 1993). Treatment of mice with anti-Fas monoclonal agonistic antibody induces apoptosis of hepatocytes, leading to animal death of within several hours. The study included intravenous administration of DDC to anti-Fas-Ab-injected mice, as well as to control, untreated animals. Fluorescence histopathological studies were then performed to evaluate the level of DDC binding.

Five-week-old male BALB/c mice were injected intravenously with 10 μg/animal of purified hamster anti-Fas mAb (Jo2, PharMingen, San Diego, Calif.). Mice were then injected intravenously with 70 mg/Kg of DDC. Injections were performed 30 minutes after antibody treatment. Control animals were injected with DDC only, without antibody administration. All animals were sacrificed three hours after administration of the antibody, followed by organ removal. Liver was sectioned transversely across the mid-portion of each lobe, dipped immediately into liquid nitrogen, and then transferred to −80° C. for 24 hours. Organs were then transferred into OCT solution, and cryosections (5 μm) were prepared. These sections were taken for fluorescent microscopy. Parallel sections were stained with hematoxylin/eosin (H&E), for simultaneous evaluation; of the characteristic apoptotic morphology of the cells manifesting DDC binding.

Figure 5A:
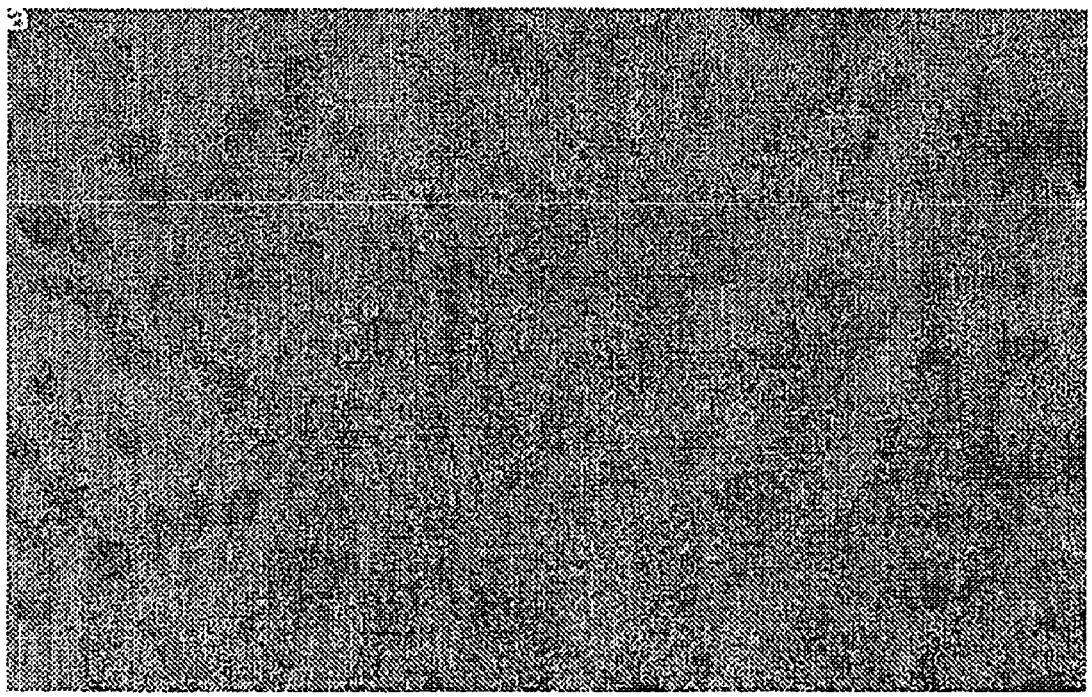
FIG. 5: Detection of liver-cell apoptosis in vivo with DDC.
Figure 5B:
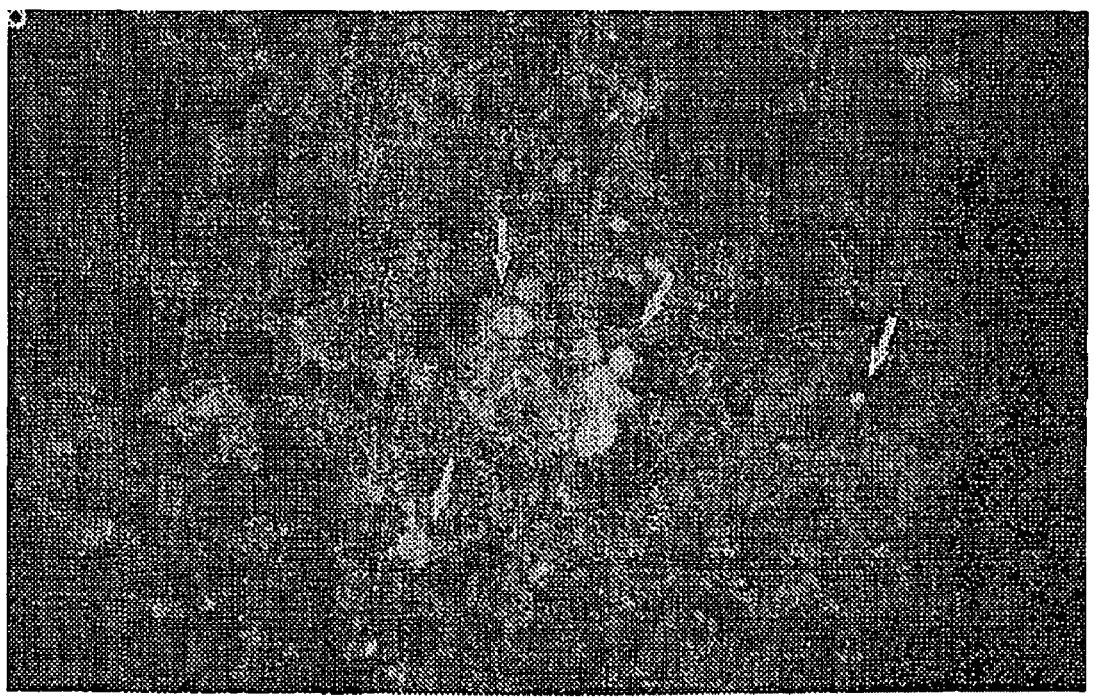

Control animals, injected with DDC did not manifest significant fluorescence in the liver sections, i.e., no significant binding of DDC was observed (FIG. 5A). By contrast, marked, specific binding of DDC to numerous apoptotic cells was observed in the livers from animals treated with the anti-Fas Ab (FIG. 5B; arrows mark several of the apoptotic cells). Comparison with the H&E staining confirmed the indeed the cells which manifested DDC binding had characteristic apoptotic morphology.

These experiments therefore demonstrate the potential of DDC, upon systemic administration, to detect and selectively bind to apoptotic cells in vivo.

Example 6

Detection of Apoptotic Cells In Vivo within a Tumor by DDC

One of the characteristics of primary tumors is the occurrence of tumor cell apoptosis, in parallel to the proliferation of the neoplastic cells. It is clear now, that the net balance between proliferation and apoptosis within a primary tumor is an important prognostic factor and a predictor of metastases (Naresh, K. Y., et al., *Cancer*, 91: 578-594, 2001). A high prevalence of apoptotic cells is associated with a more malignant tumor and poorer prognosis. Therefore, a non-invasive diagnostic and predictive tool to evaluate the apoptotic load within a tumor in-vivo has potential important applications in clinical oncology.

DDC was therefore used to detect apoptotic cells within tumors. Primary tumors of Lewis Lung carcinoma (3LL) were induced in 12 weeks old c57 black mice by subcutaneous injection of $0.5 \times 10^6$ cells/animal of D122 tumor cells. Tumor cell line was maintained as described by Eisenbach L, et al., (*Int. J. Cancer*, 34:567-573, 1984). Two weeks following the injection, when tumors of 2-3 mm were observed, animals were injected intravenously with 70 mg/kg of DDC, Tumor was removed two hours later, and quickly frozen in liquid nitrogen. Cryo-sections were then prepared and subjected to histopathological analysis, using a fluorescent microscope (magnification ×600).

The ability of DDC to detect apoptotic cells within the tumor upon systemic administration in-vivo, is demonstrated in FIG. 6A. Such detection allows for calculation of the apoptotic index (AI) of the tumor. In order to demonstrate that this index, achieved with the DDC does indeed reflect the apoptotic load within the tumor, a parallel staining with TUNEL, a well-accepted method for detection of the characteristic apoptotic internucleosomal DNA cleavage was used (FIG. 6B). Similar number of apoptotic cells can be observed within the tumor, using both detection methods. DDC is therefore capable of detecting the apoptotic load within a tumor in vivo. Its sensitivity in measuring the AI of the tumor in vivo, upon systemic intravenous administration, is similar to the direct characterization achieved by the TUNEL procedure on tissue sections ex-vivo.

Example 7

Detection by NST750 of Chemotherapy-Induced Apoptosis of Small Intestine Epithelium Gastrointestinal damage is often observed during chemotherapy administration to a cancer patient. In particular, the small intestine manifest apoptosis of epithelial cells as an early response to chemotherapy and irradiation (Keefe, D. M. K., et al., *Gut*, 47:632-637, 2000). The NST750 compound was therefore evaluated for its ability to detect the apoptotic process in vivo, in the small intestine of healthy mice, treated with a single dose of chemotherapy.

Twelve-week old Balb/c mice or Swiss mice were treated intravenously with a single dose of a combination of Taxol (300 mg/kg) and cyclophosphamide (27 mg/kg). Animals that did not receive chemotherapy served as controls. After 24 hours, all animals were injected intravenously with 13 mg/kg of NST750. Two hours later, animals were sacrificed, the small intestine was frozen, and cryo-sections were prepared for fluorescent microscopy.

Figure 7A:
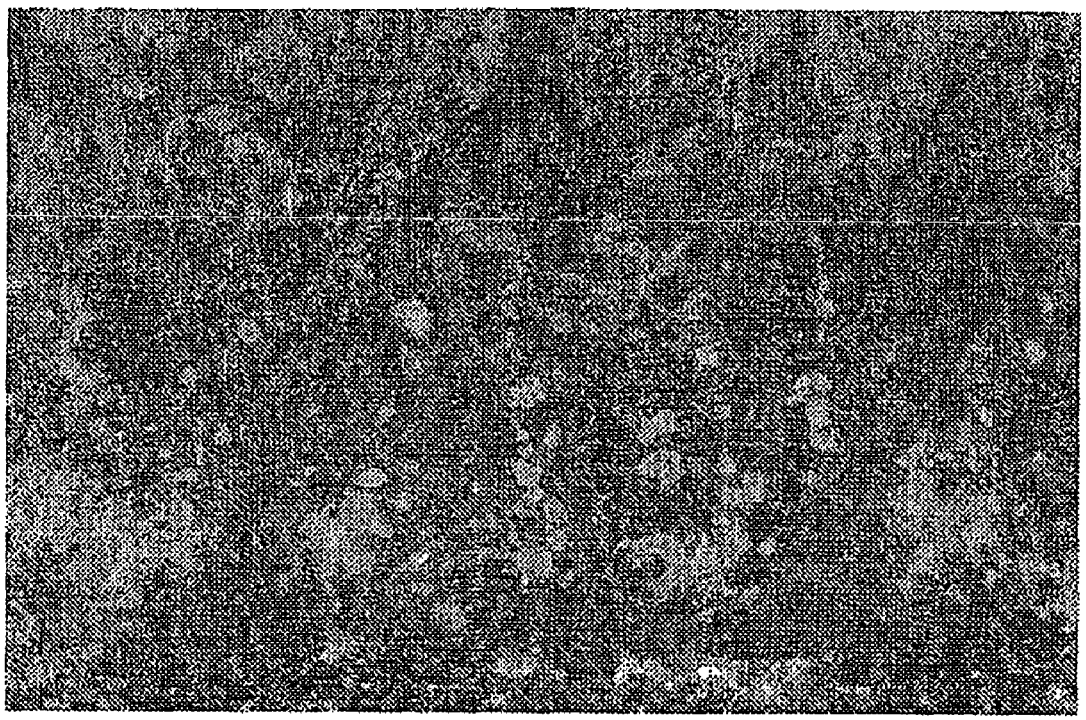
FIG. 7: Detection of chemotherapy-induced apoptosis of small intestine is epithelial cells in vivo by NST750.
Figure 7B:

Multiple apoptotic cells, strongly binding NST750 were detected in the small intestinal crypts of the chemotherapy-treated mice (FIG. 7A). By contrast, no significant staining with NST750 was observed in the control non-treated is animals (FIG. 7B). NST750 therefore manifested selective binding and detection of apoptosis induced by chemotherapy in small intestine epithelial cells. This provides a tool for an early and sensitive monitoring (only 24 hours after a single dose of anti-cancer treatment) of this adverse effect of chemotherapy. This activity of NST750 may therefore have important clinical applications in the optimization of anti-cancer treatments.

Example 8

Synthesis of NST750

NST750 was synthesized according to the following Scheme:

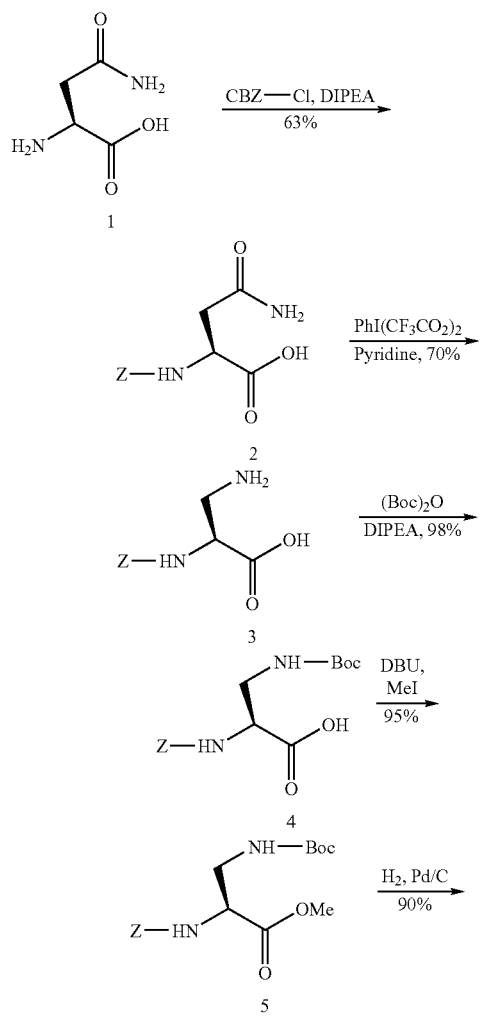

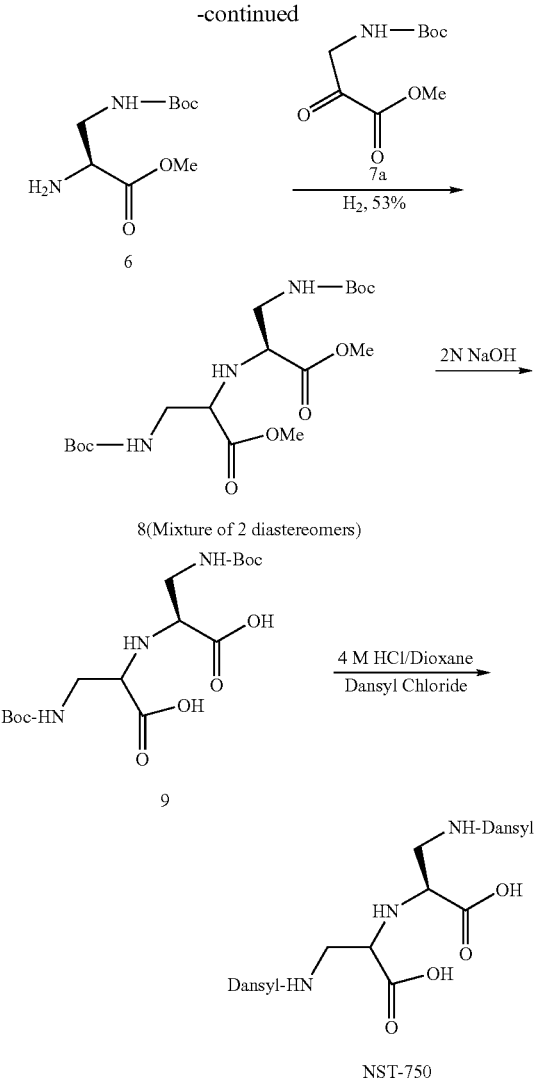

L-asparagine was reacted with carbobenzoxy (Z) chloride, in the presence of diisopropylethylamine (DIPEA) in 63% yield. Z-protected asparagine 2 (50 g) 10 in a mixture of 500 mL of dimethyl formamide (DMF), containing 100 mL of water, cooled to 0° C., was treated all at once with 85 g of bis-trifluoroacetoxyiodobenzene. After stirring at 0° C. for 10 minutes, the reaction was treated dropwise with 3 mL of pyridine over a period of 15 minutes. The solution was stirred at RT overnight. The reaction was concentrated in vacuo at 45° C., and the resulting oil was dissolved in a mixture of 500 mL of water and 200 mL of ethanol. The pH of the solution was adjusted to 5.0 with pyridine and the resulting voluminous precipitate collected by vacuum filtration. The solid was washed with 200 mL of dichloromethane and dried in vacuo at 40° C. to provide 3 (31 g) in 70% yield. Z-protected derivative 3 (31 g) was converted to intermediate 4 in 80% yield. Similarly, application of iodomethane in the presence of diazabicycloundecene (BDU) afforded methyl ester 5 almost quantitatively. 2-Amino-4-Boc amino methyl butyrate (6) was obtained after removal of the Z-protective group by hydrogenation.

Isoserine 11 was added to a preformed solution of methanol and acetyl chloride under nitrogen. After refluxing for 2 hours, the reaction was judged complete. The reaction mixture was concentrated to dryness and the resulting oil dissolved in a mixture of methanol/dioxane, treated with DIPEA, followed by the addition of butyloxycarbonyl (Boc)-anhydride. After usual workup, the crude reaction mixture was purified by flash column chromatography using 30% EtOAc/Heptane as the eluant to provide 13 in 95% yield. Compound 13 was then subjected to oxidation using Dess Martin reagent to provide 2-keto-4-Boc amino methyl butyrate 7a in 60% yield.

Reductive coupling of keto-ester 7a was performed at 40° C. in the presence of 1.3-1.5 equivalents of amine 6 acetic acid and magnesium sulfate. Subsequent hydrogenation (palladium on charcoal, 50 psi, 12 hrs.) resulted in 8 as a mixture of diastereomers (53% yield).

nesium sulfate. After concentration to dryness, 160 mg of a bright yellow solid was isolated. The solid was crystallized from a mixture of methanol/ether to afford 100 mg of a yellow solid imino-bis 2-(3-dansyl amido)-propionic acid (NST 750). $^1$H NMR (300 MHz, CD$_3$OD), δ 8.58 (bm, 2H), 8.478.2 (b, 4H), 7.6 (b, 4H), 7.25 (b, 2H) 3.5-3.0 (b, 4H), 2.9 (s, 12H), 1.4 (m, 2H). MS (ESI) 658.2) (M+H).

Example 9

Synthesis of NST740

NST740 was synthesized according to the following scheme:

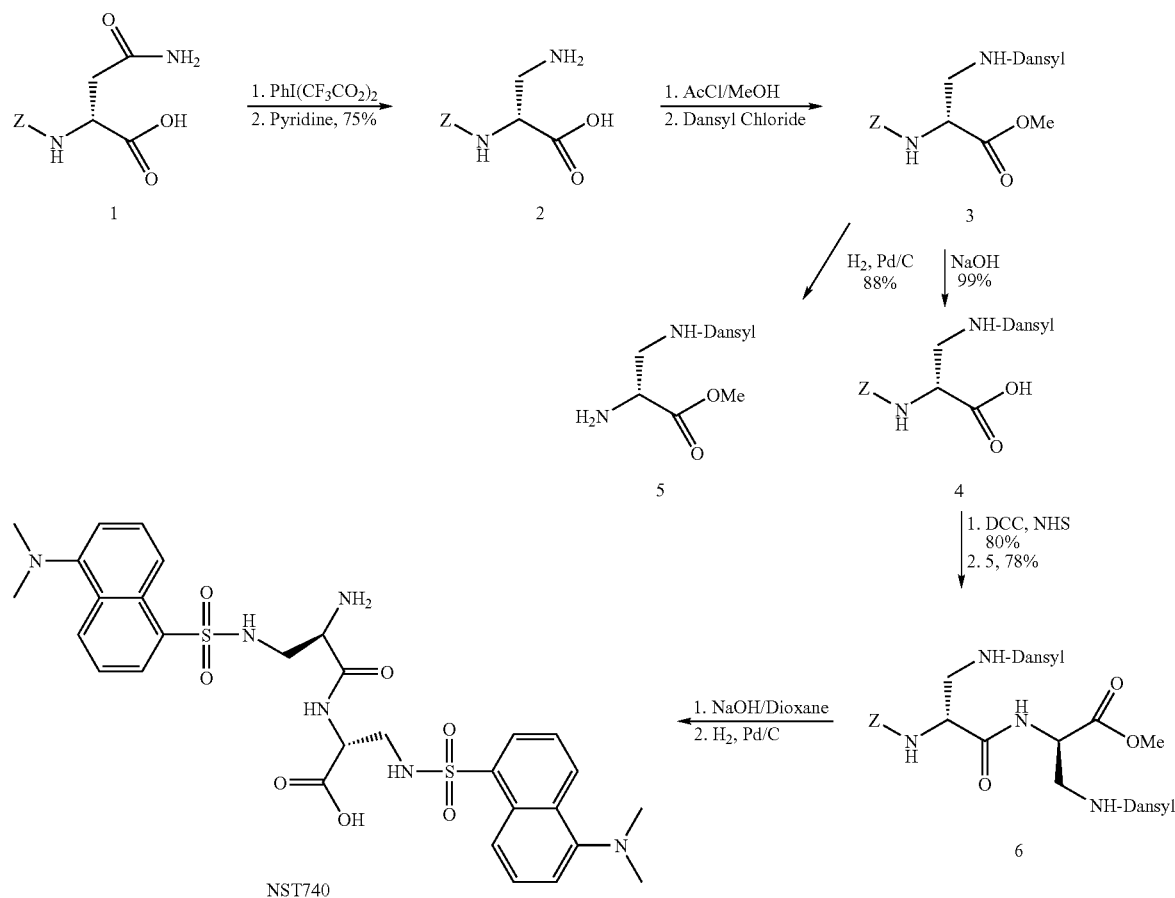

Compound 8 (0.25 g), being a mixture of diastereomers was submitted to the hydrolysis of the methyl ester using 2N NaOH in dioxane at RT for 2 hours. The reaction mixture was further concentrated to dryness to afford 0.4 g of a white solid. The corresponding solid was suspended in 6 mL of dioxane and treated with 5 mL of 2M HCl/Ether solution. The reaction was then concentrated, the residue was dissolved in water/dioxane, and the pH was adjusted to 9.2 with DIPEA. The resulting solution was treated with a solution of dansyl chloride (2 eq.), while simultaneously keeping the pH of the reaction around 9.2. After completion, the reaction was diluted with water (10 mL) and washed with ether. The ether layer was discarded and the aqueous layer covered with ethyl acetate and acidified to pH 4.0 with 2 M HCl. The organic layer was washed with brine, and dried over anhydrous mag- Carbobenzoxy (cbz)-D-asparagine 1 was converted, in very good yield to 2-cbz protected 2,3-diaminopropionic acid 2 using bis-trifluoroacetoxyiodobenzene. 2 (7.2 g) was refluxed in a solution of acetyl chloride and methanol to provide quantitative yield of the methyl ester hydrochloride salt. That salt was further suspended in anhydrous dichloromethane and treated with 2.5 equivalents of triethylamine. Once a clear solution was obtained, the resulting solution was treated with a solution of dansyl chloride. After stirring at RT overnight, the reaction was complete. The reaction mixture was diluted with 100 mL of Dichloromethane (DCM) and successively washed with aqueous saturated sodium bicarbonate (2×100 mL), water (100 mL) and brine. The resulting organic solution was dried (MgSO$_4$), and concentrated to dryness. The resulting oil was chromatographed over silica gel (10% EtOAc/CHCl₃) to provide 3 in 72% yield. A portion of this material (3.5 g) was subjected to the hydrolysis in a mixture of Tetrahydrofuran(THF)/MeOH to provide after a common work-up 3.4 g of 4 as a bright yellow solid. Simultaneously, 5.6 g of 3 were submitted to removal of the benzyl carbamate to provide the amino ester. 5 in good yield. Treatment of 4 (0.5 g) with 1 equivalent of dicyclohexylcarbodiimide (DCC) and N-hydroxy succinimide (NHS) for 5 hours resulted in complete conversion to the desired NHS ester in 83% yield. That ester was further dissolved in anhydrous THF and treated with an equimolar amount of 5. After 6 hrs, the reaction mixture was diluted with ethyl acetate and washed with saturated NH₄Cl to remove the NHS by-product. The organic layer was further dried over magnesium sulfate and concentrated to dryness to afford 0.8 g of the dipeptide 6 in 77% yield which was >95% pure by HPLC analysis. The methyl ester was subsequently hydrolyzed in sodium hydroxide in dioxane, and the carbobenzoxy protecting group was removed in the usual manner (H₂/Pd) to afford 2-(3-dansylamido-2-aminopropioncarboxamido)-3-dansylamido-propionic acid (NST740). ¹H NMR (300 MHz, CD₃OD), δ 8.53 (dd, 2H, J=8.5, 8.6 Hz), 8.34 (d, J=8.67 Hz, 1H), 8.24 (dd, J=8.6, 7.3 Hz, 2H), 8.12(d, 7.32 Hz, 1H), 7.5 (m, 4H), 7.26 (d, J=7.56 Hz, 1H), 7.19 (d, J=6.98 Hz, 1H), 4.18 (t, J=4.34 Hz, 1H), 3.65 (t, J=3.45 Hz, 1H), 3.2 (m, 4H), 2.85 (s, 12H). MS (ESI) 657.16 (M+H).

Example 10

Synthesis of NST751

NST751 was synthesized according to the following Scheme:

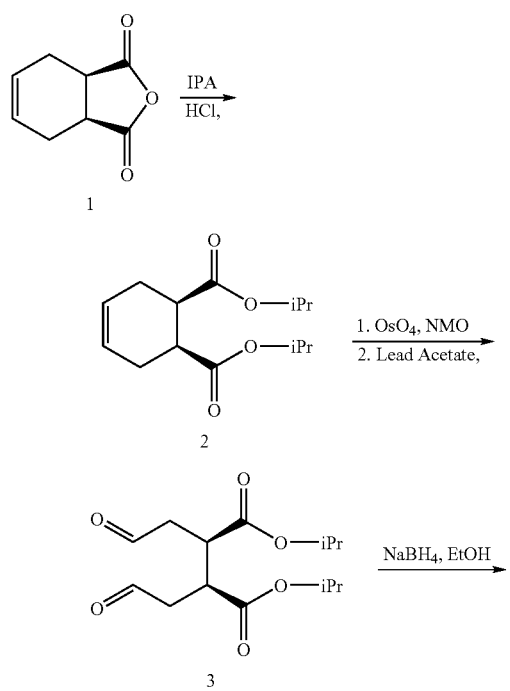
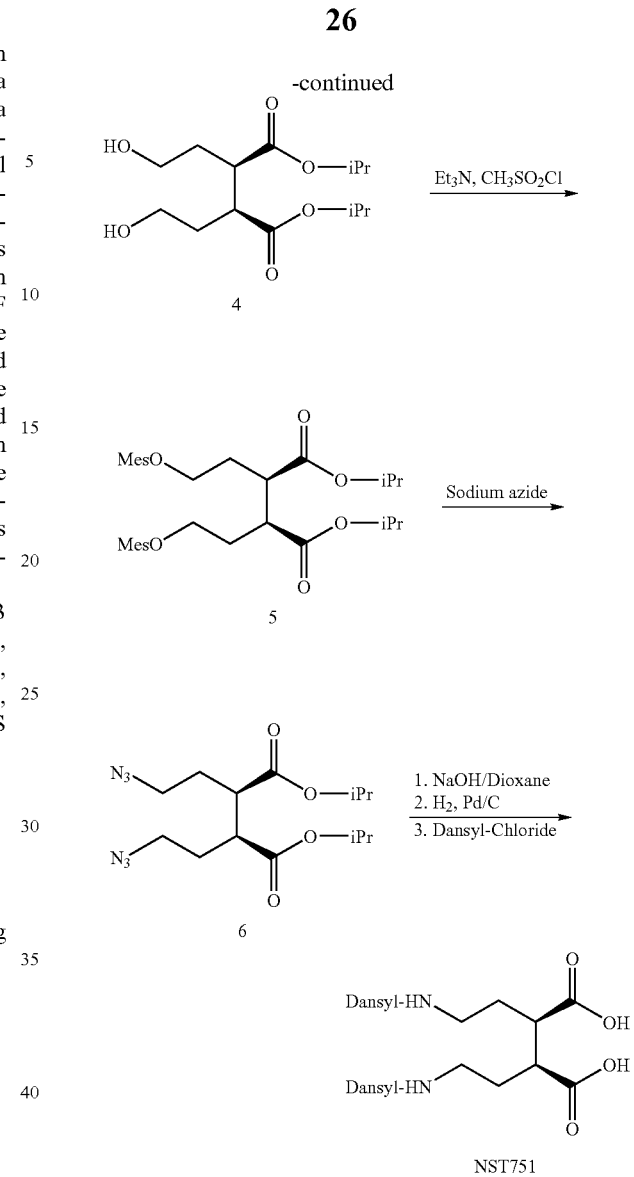

4-Cyclohexene-1,2-dicarboxy anhydride 1 (30 g) was refluxed in toluene with a catalytic amount of sulfuric acid along with 10 equivalents of isopropyl alcohol. After stirring at reflux for 6 hours, 30 g of diisopropyl-4-cyclohexene-1,2-succinate 2 was isolated. Compound 2 (7 g) was submitted to the oxidative cleavage using osmium tetroxide followed by lead acetate. After a common work up, 7 g of the diisopropyl bis 1,2(2-acetaldehyde)meso succinate 3 was obtained and used directly in the next step. Compound 3 (6.8 g) was dissolved in ethanol and treated with 1 equivalent of sodium borohydride. After stirring at 0° C. for 1 hour, the reaction was completed (R_f 3 0.4, R_f 4 0.1:40% EtOAc/Heptane) and carefully quenched by the addition of 1M HCl. The organic layer was removed in vacuo and the aqueous layer extracted with ethyl acetate. After drying over magnesium sulfate and concentration in vacuo, diisopropyl bis 1,2(2-ethanol)meso succinate 4 (6.8 g) was obtained in 90% yield. ¹H NMR 1.3 ppm (14H, isopropyl ester), 3.6 ppm (4H, hydroxymethyl).

Diol 4 (6.8 g) was dissolved in anhydrous dichloromethane and treated with 3 equivalents of triethylamine followed by the slow addition of 2 equivalents of methanesulfonyl chloride at 0° C. for two hours. The reaction mixture was quenched with the addition of saturated ammonium chloride solution and the organic layer collected, washed with brine, dried over magnesium sulfate and filtered. Concentration of the filtrate to dryness was followed by silica gel chromatography to afford diisopropyl bis 1,2(2-methanesufonylethyl) meso succinate 5 (4 g) in 55% yield.

Bis-mesylate 5 was treated with sodium azide in dimethylformamide (DMF) at 40° C. for 3 hours. After usual work up, diisopropyl bis 1,2 (2-azidolethyl)meso succinate 6 was isolated in 93% yield, Compound 6 (2.1 g) was dissolved in a mixture of ethanol/water (3:1) and treated with sodium hydroxide (2 eq) at 30° C. overnight. The reaction was diluted with water, the bulk of ethanol removed in vacuo and the aqueous layer washed with ether. The aqueous layer was covered with ethyl acetate (100 mL) and acidified to pH 2.5 with 3M HCl. After concentration in vacuo, 1.5 g of the bis-acid was obtained. The resulting azido-acid was dissolved in a mixture of ethanol/2M NaOH (10:1) and hydrogenated at 50 psi of hydrogen over palladium on charcoal for two hours. Conversion to the diamine was completed and the reaction mixture was filtered over Celite and the filtrate concentrated to dryness to afford 1.5 g of a sticky solid, which was subsequently reacted with dansyl chloride to afford bis-1,2-(dansyl-3-aminoethyl)meso succinic acid (NST751). $^1$H NMR (300 MHz, CD$_3$OD), δ 8.50 (d, J=8:6 Hz, 2H). 8.35 (d, J=8.8 Hz, 2H), 8.15 (t, J=4.5 Hz, 2H), 7.51 (m, 4H), 7.19 (d, J=8.3 Hz, 2H), 2.87 (s, 12H), 2.75 (m, 4H), 2.3 (m, 1H), 2.2 (m, 1H), 1.5 (m, 2H), 1.29 (m, 2H). MS (ESI) 671.0 (M+H).

The invention claimed is:

1. A compound having the chemical formula

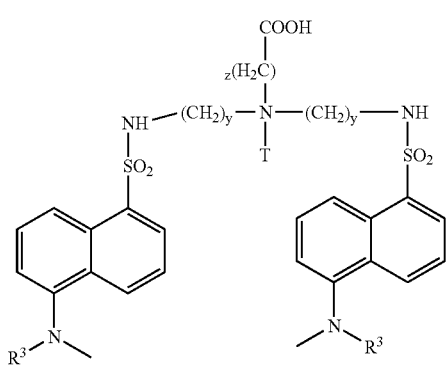

(VII)

wherein y is an integer of 2 to 6; z is an integer of 1 to 6; z is an integer of 1 to 6; T is selected from null, hydrogen and methyl; and R$^3$ represents hydrogen or (C$_1$-C$_6$) alkyl.

2. A compound having the chemical formula

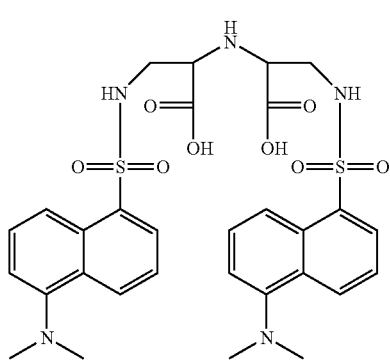

(VIII)

and/or pharmaceutically acceptable salts and hydrates thereof.

3. A compound having the chemical formula

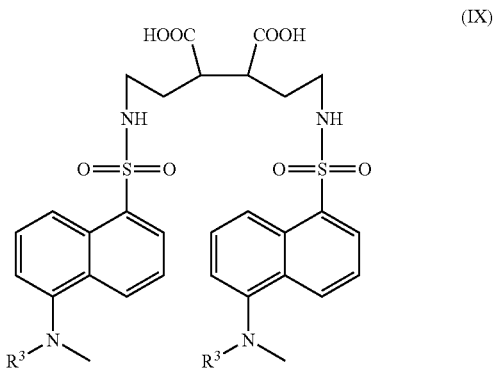

(IX)

and/or pharmaceutically acceptable salts and/or hydrates thereof, wherein R$^3$ represents hydrogen or methyl.

4. A method for selectively binding a perturbed membrane-binding compound (PMBC) to a perturbed membrane in a cell(s), tissue(s) or cellular structure(s), comprising contacting a PMBC having the chemical formula

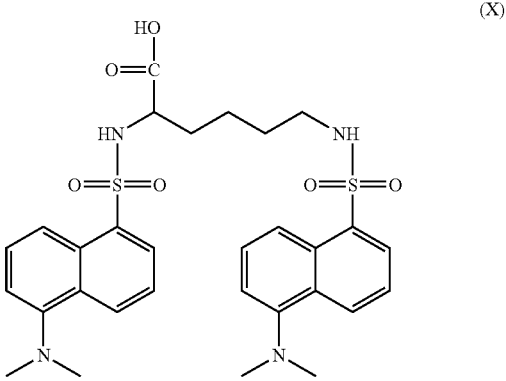

(X)

and/or pharmaceutically acceptable salts and/or hydrates thereof, with a cell(s), tissue(s) or cellular structure(s) comprising a perturbed membrane(s) so that said PMBC binds to said perturbed membrane(s).

* * * * *